(12) United States Patent
Mauch et al.

(10) Patent No.: US 8,834,499 B2
(45) Date of Patent: Sep. 16, 2014

(54) PERCUTANEOUS METHODS AND APPARATUS FOR CREATING NATIVE TISSUE VENOUS VALVES

(71) Applicant: Medtronic Vascular, Inc., Santa Rosa, CA (US)

(72) Inventors: Kevin Mauch, Windsor, CA (US); Maria Arreguin, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 23 days.

(21) Appl. No.: 13/892,573

(22) Filed: May 13, 2013

(65) Prior Publication Data
US 2013/0253553 A1 Sep. 26, 2013

Related U.S. Application Data

(62) Division of application No. 12/767,938, filed on Apr. 27, 2010, now Pat. No. 8,460,323.

(51) Int. Cl.
| | |
|---|---|
| *A61B 17/32* | (2006.01) |
| *A61B 17/3207* | (2006.01) |
| *A61M 25/10* | (2013.01) |
| *A61B 8/08* | (2006.01) |
| *A61F 2/24* | (2006.01) |
| *A61B 17/3209* | (2006.01) |
| *A61B 17/22* | (2006.01) |
| *A61B 8/12* | (2006.01) |
| *A61B 17/00* | (2006.01) |
| *A61M 25/01* | (2006.01) |

(52) U.S. Cl.
CPC ...... *A61B 17/320725* (2013.01); *A61M 25/104* (2013.01); *A61B 8/0841* (2013.01); *A61F 2/2475* (2013.01); *A61M 2025/1081* (2013.01); *A61B 17/3209* (2013.01); *A61M 2025/1075* (2013.01); *A61B 2017/22061* (2013.01); *A61M 25/10* (2013.01); *A61B 8/12* (2013.01); *A61B 2017/00783* (2013.01); *A61F 2/2463* (2013.01); *A61M 25/0105* (2013.01)
USPC ................................................ 606/159

(58) Field of Classification Search
USPC ......... 606/159, 167, 170, 172, 185, 190, 191, 606/194, 198; 623/2.11
See application file for complete search history.

(56) References Cited

U.S. PATENT DOCUMENTS

| | | | |
|---|---|---|---|
| 5,464,395 | A | 11/1995 | Faxon et al. |
| 5,697,944 | A | 12/1997 | Lary |

(Continued)

FOREIGN PATENT DOCUMENTS

| | | |
|---|---|---|
| EP | 0611582 | 8/1994 |
| WO | WO95/26776 | 10/1995 |
| WO | WO01/49357 | 7/2001 |

OTHER PUBLICATIONS

U.S. Appl. No. 12/335,786, filed Dec. 16, 2008.

(Continued)

*Primary Examiner* — Ryan Severson

(57) ABSTRACT

Percutaneous methods and apparatuses for forming a venous valve from autologous tissue. A catheter having a retractable dissecting system received therein is delivered to a target location where a new venous valve is to be created. A distal balloon or other radially-expandable component mounted on the catheter is expanded against the vein wall, and the dissecting system is proximally retracted to deploy one or more dissecting components that dissect a subintimal layer of the vein wall. Radial expansion of the dissecting component(s) within the vein wall creates one or more leaflets and corresponding pocket/sinuses in the vein that collectively act as a venous valve, and/or the radially-expandable component of the catheter is subsequently collapsed such that the dissecting component(s) each pull a flap of the dissected tissue towards the vein lumen to create one or more leaflet(s) and corresponding pocket/sinuses in the vein.

11 Claims, 17 Drawing Sheets

(56) References Cited

U.S. PATENT DOCUMENTS

| | | |
|---|---|---|
| 6,165,187 A | 12/2000 | Reger |
| 6,190,353 B1 | 2/2001 | Makower et al. |
| 6,902,576 B2 | 6/2005 | Drasler et al. |
| 7,008,411 B1 | 3/2006 | Mandrusov et al. |
| 7,029,483 B2 | 4/2006 | Schwartz |
| 7,150,738 B2 | 12/2006 | Ray et al. |
| 7,163,546 B2 | 1/2007 | Mirizzi et al. |
| 7,517,352 B2 | 4/2009 | Evans et al. |
| 7,955,346 B2 | 6/2011 | Mauch et al. |
| 8,177,802 B2 | 5/2012 | Mauch et al. |
| 2003/0125759 A1 | 7/2003 | Mirizzi et al. |
| 2011/0264127 A1 | 10/2011 | Mauch et al. |

OTHER PUBLICATIONS

U.S. Appl. No. 12/335,804, filed Dec. 16, 2008.
U.S. Appl. No. 12/767,932, filed Apr. 27, 2010.
Dalsing, Michael, "Prosthetic Venous Valves" The Vein Book, Chp 64, pp. 593-598, 2006.
Peruzzi et al., "A New Autologous Venous Valve by Intimal Flap" Minerva Cardioangiologica, vol. 51, No. 4, p. 395, Aug. 2003.
Maleti et al., "Neovalve Construction in Postthrombotic Syndrome" The Journal of Vascular Surgery, vol. 43, No. 4, pp. 794-799, 2006.
Non-Final Office Action Dated Jun. 20, 2012 for U.S. Appl. No. 12/767,932 to Mauch et al., filed Apr. 27, 2010.
Reply/Amendment Dated Sep. 20, 2012 for U.S. Appl. No. 12/767,932 to Mauch et al., filed Apr. 27, 2010.

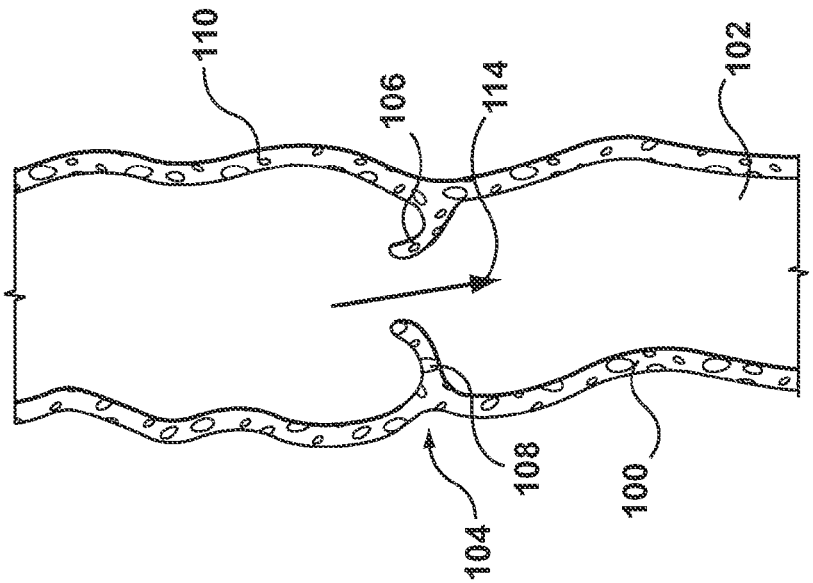
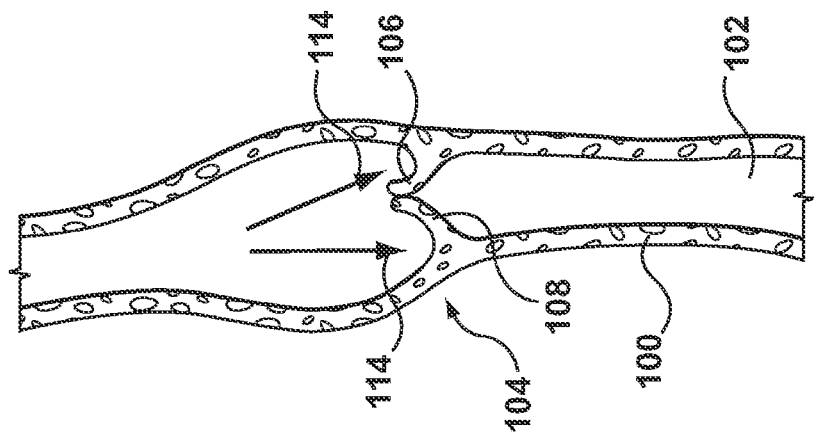
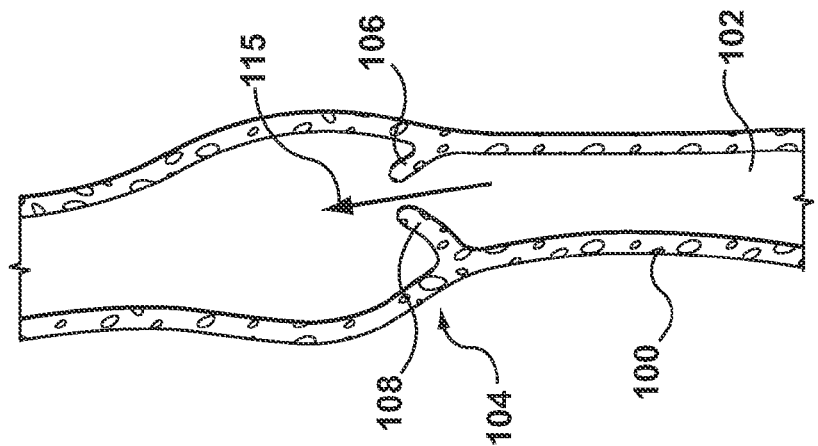

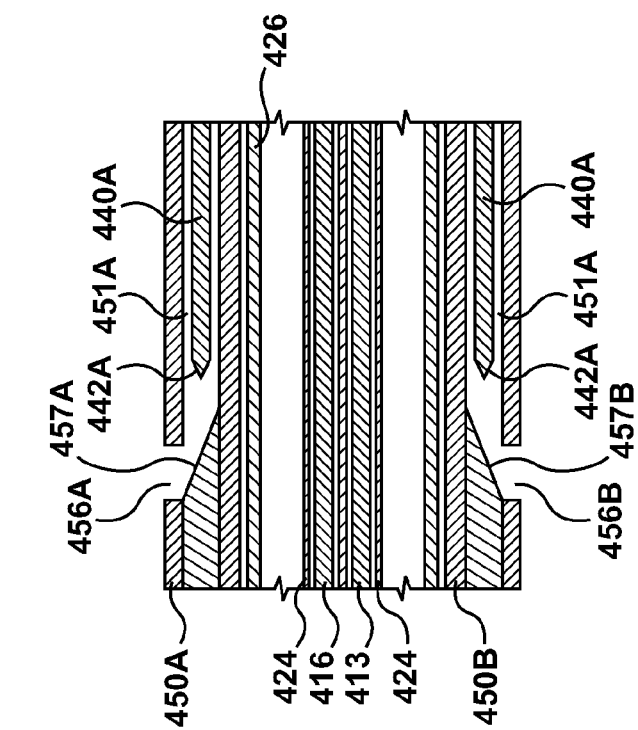
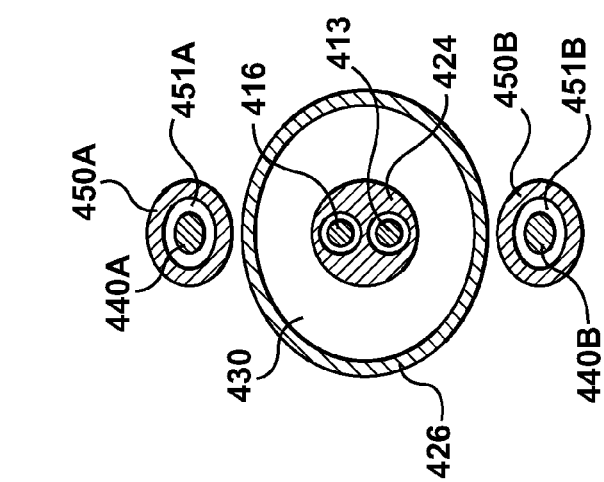
FIG. 4A  FIG. 4B  FIG. 4C  FIG. 4D

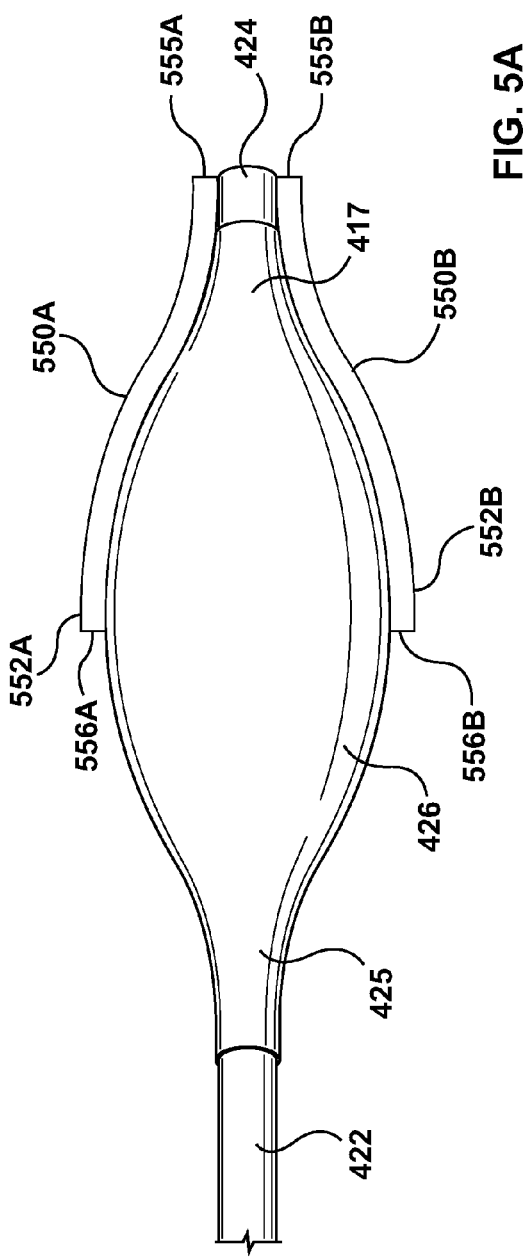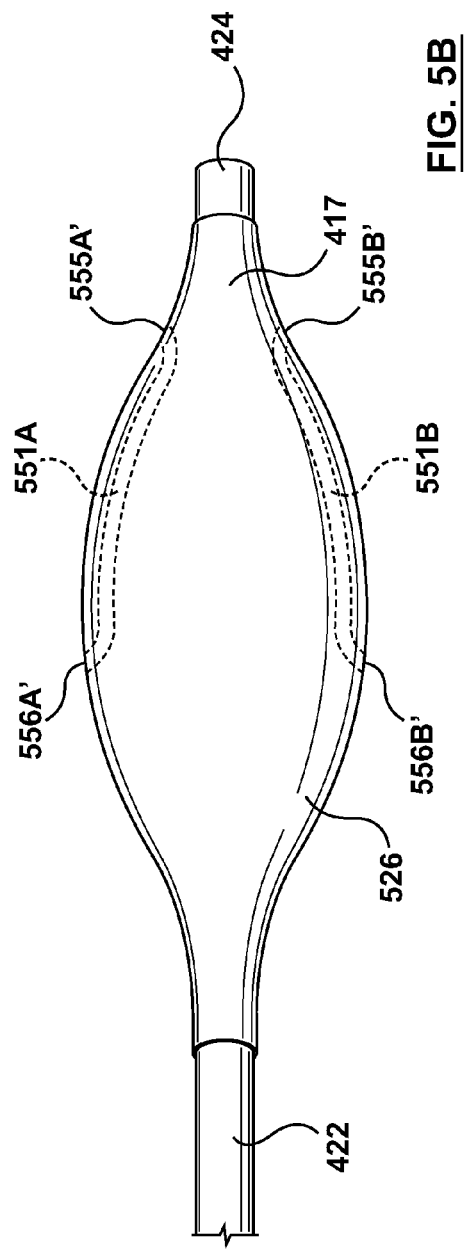

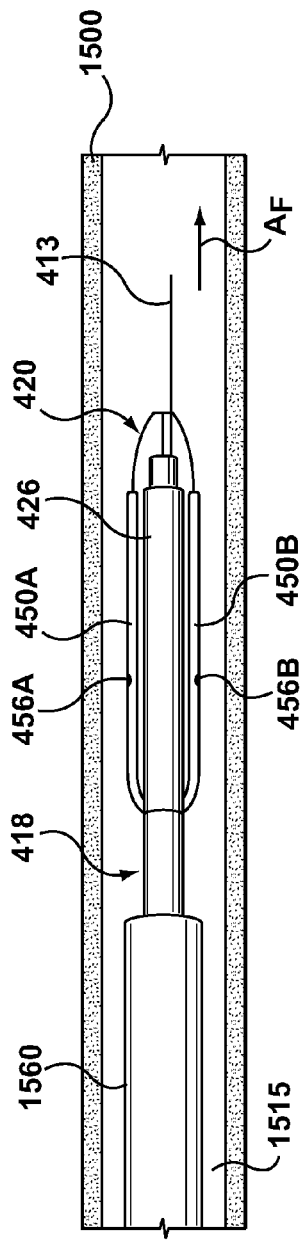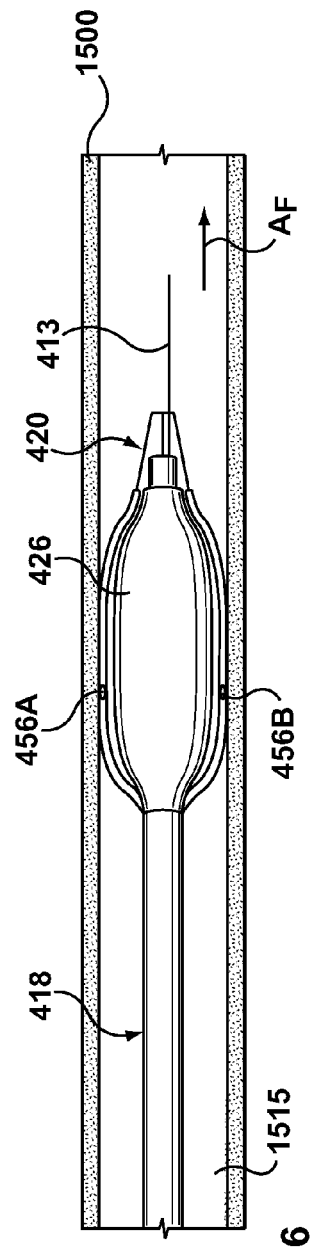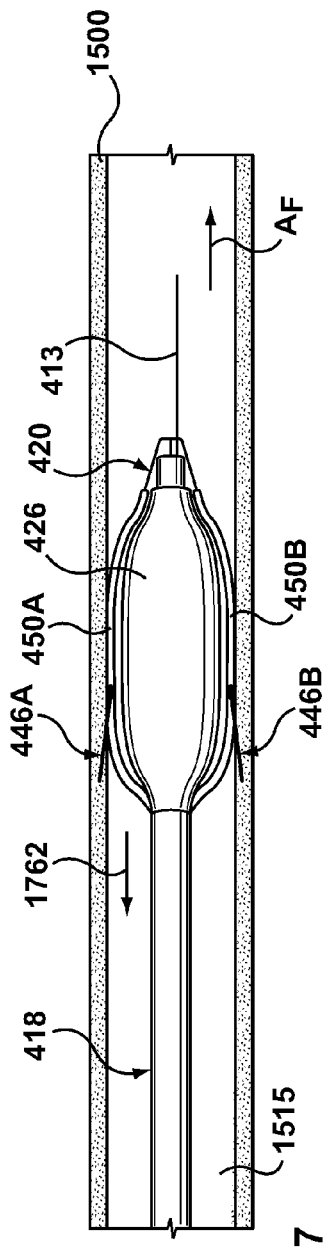

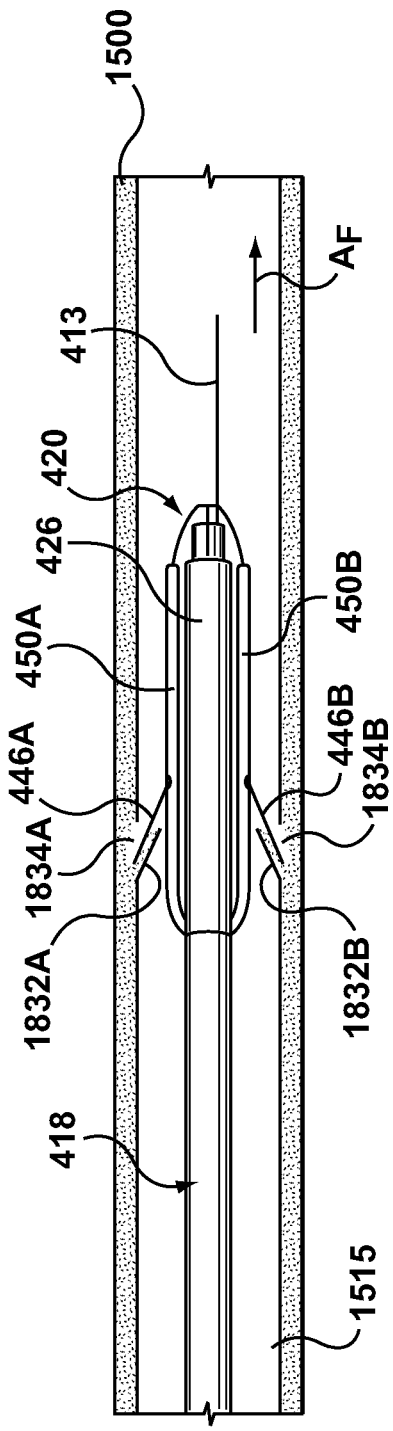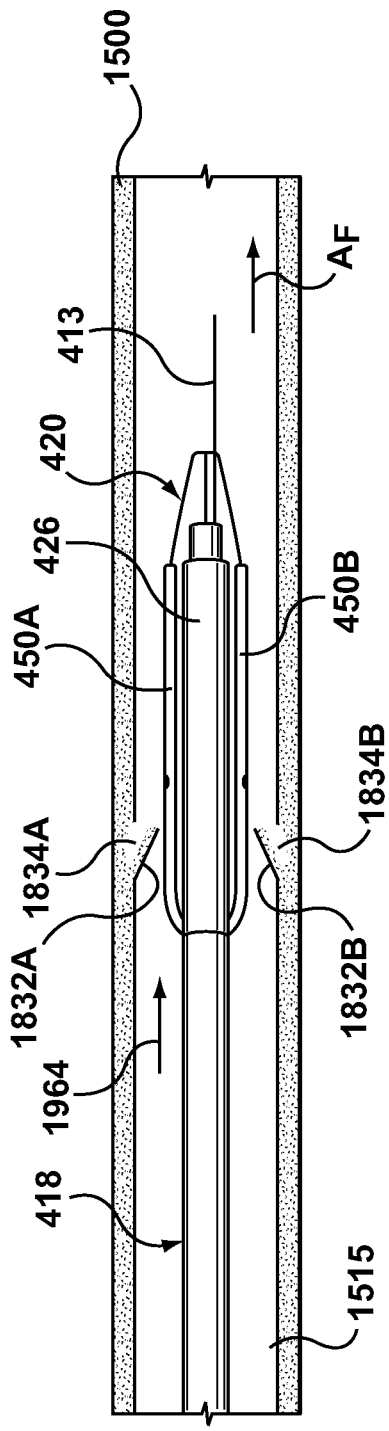

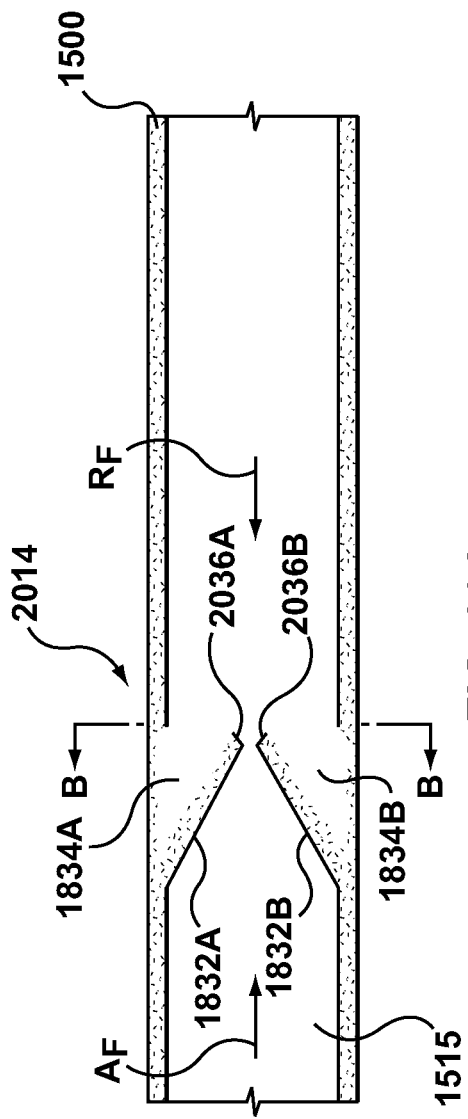
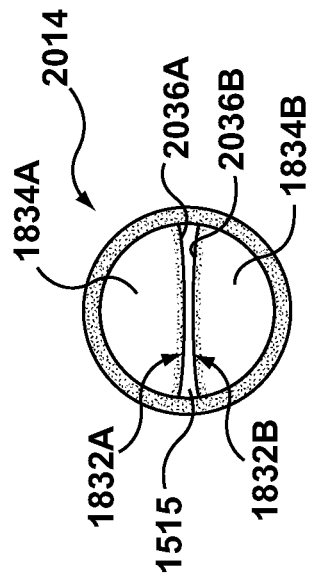
FIG. 20A
FIG. 20B

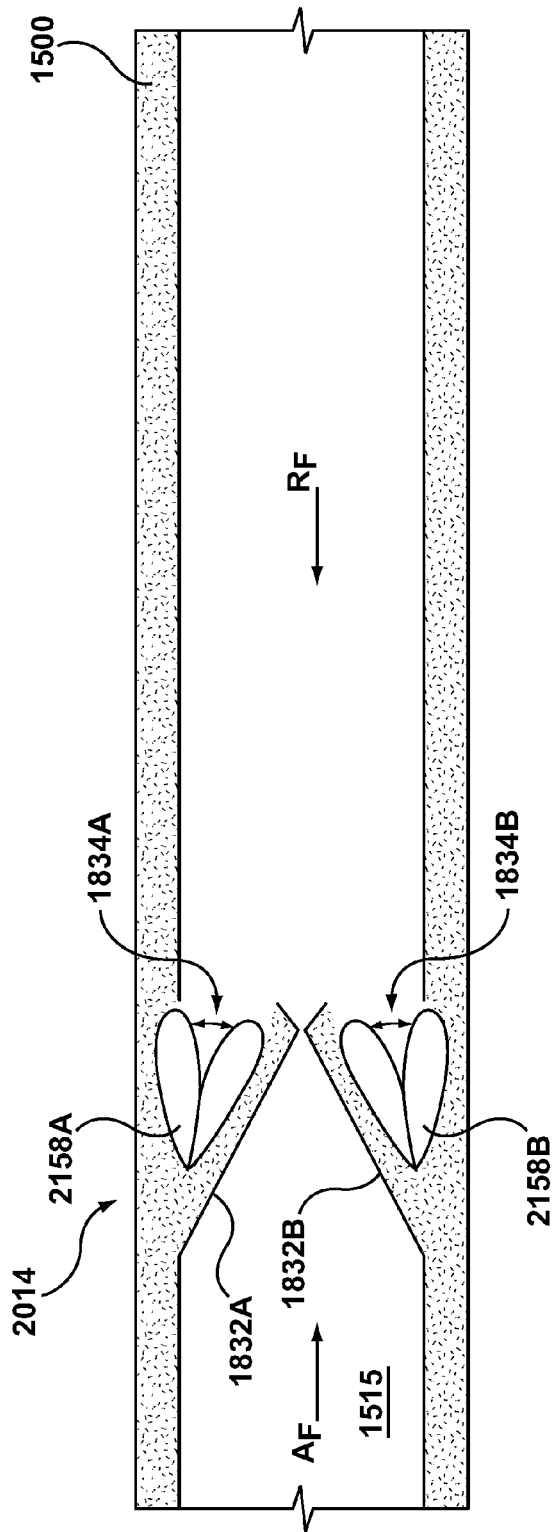
FIG. 21
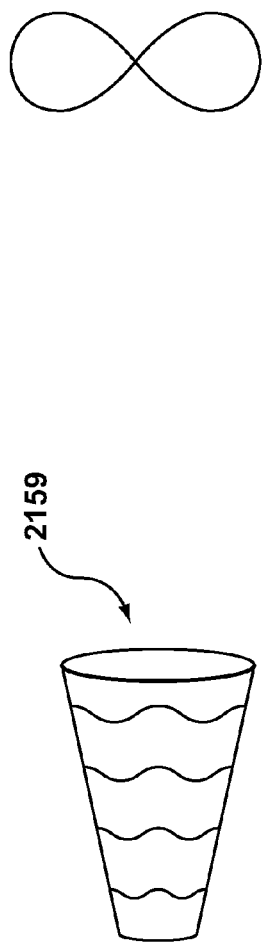
FIG. 21A
FIG. 21B

PERCUTANEOUS METHODS AND APPARATUS FOR CREATING NATIVE TISSUE VENOUS VALVES

RELATED APPLICATIONS

This application is a Division of and claims the benefit of U.S. patent application Ser. No. 12/767,938 filed Apr. 27, 2010. The disclosures of which are herein incorporated by reference in their entirety.

FIELD OF THE INVENTION

The invention relates to apparatus and methods for percutaneously creating a one-way venous valve in vivo from autologous tissue.

BACKGROUND OF THE INVENTION

Venous valves are found within native venous vessels and are used to assist in returning blood back to the heart in an antegrade direction from all parts of the body. The venous system of the leg includes the deep venous system and the superficial venous system, both of which are provided with venous valves that are intended to direct blood toward the heart and prevent backflow or retrograde flow, which can lead to blood pooling or stasis in the leg in the setting of incompetent valves. Incompetent valves can also lead to reflux of blood from the deep venous system to the superficial venous system and the formation of varicose veins. Superficial veins, which include the greater and lesser saphenous veins, have perforating branches in the femoral and popliteal regions of the leg that direct blood flow toward the deep venous system and generally have a venous valve located near the junction with the deep system. Deep veins of the leg include the anterior and posterior tibial veins, popliteal veins, and femoral veins. Deep veins are surrounded in part by musculature tissue that assists in generating flow due to muscle contraction during normal walking or exercising. Veins in the lower leg have a static pressure while standing of approximately 80-90 mm Hg that may reduce during exercise to 60-70 mm Hg. Despite exposure to such pressures, the valves of the leg are very flexible and can close with a pressure drop of less than one mm Hg.

FIGS. 1A-1B are schematic representations of blood flow through a healthy native valve 104 within a vein 100. Venous valve 104 controls blood flow through lumen 102 of vein 100 via leaflets 106, 108. More particularly, venous valve 104 opens to allow antegrade flow 112 through leaflets 106, 108 as shown in FIG. 1A. Venous valve 104 closes to prevent backflow or retrograde flow 114 through leaflets 106, 108 as shown in FIG. 1B.

Veins typically in the leg can become distended from prolonged exposure to excessive pressure and due to weaknesses found in the vessel wall causing the natural venous valves to become incompetent leading to retrograde blood flow in the veins. Such veins no longer function to help pump or direct the blood back to the heart during normal walking or use of the leg muscles. As a result, blood tends to pool in the lower leg and can lead to leg swelling and the formation of deep venous thrombosis, phlebitis, and varicose veins. The formation of thrombus in the veins can further impair venous valvular function by causing valvular adherence to the venous wall with possible irreversible loss of valvular function. Continued exposure of the venous system to blood pooling and swelling of the surrounding tissue can lead to post phlebitic syndrome with a propensity for open sores, infection, and may lead to possible limb amputation.

Chronic Venous Insufficiency (CVO occurs in patients that have either deep and/or superficial venous valves of their lower extremities (below their pelvis) that have failed or become incompetent due to congenital valvular abnormalities and/or pathophysiologic disease of their vasculature. As a result, these patients suffer from varicose veins, swelling and pain of the lower extremities, edema, hyper pigmentation, lipodermatosclerosis, and deep vein thrombosis (DVT). Such patients are at increased risk for development of soft tissue necrosis, ulcerations, pulmonary embolism, stroke, heart attack, and amputations.

FIG. 2 is a schematic representation of blood flow through an incompetent venous valve. Retrograde flow 114 leaks through venous valve 104 creating blood build-up that eventually may destroy the venous valve and cause a venous wall bulge 110. More specifically, the vessel wall of vein 100 expands into a pouch or bulge, such that the vessel has a knotted appearance when the pouch is filled with blood. The distended vessel wall area may occur on the outflow side of the valve above leaflets 106, 108 as shown in FIG. 2, and/or on the inflow side of the valve below leaflets 106, 108. After a vein segment becomes incompetent, the vessel wall dilates such that the fluid velocity decreases within the incompetent vein segment, which may lead to flow stasis and thrombus formation in the proximity of the venous valve.

Repair and replacement of venous valves presents a formidable problem due to the low blood flow rate found in native veins, the very thin wall structure of the venous wall and the venous valve, and the ease and frequency of which venous blood flow can be impeded or totally blocked for a period of time. Surgical reconstruction techniques used to address venous valve incompetence include venous valve bypass using a segment of vein with a competent valve, venous transposition to bypass venous blood flow through a neighboring competent valve, and valvuloplasty to repair the valve cusps. These surgical approaches may involve placement of synthetic, allograft and/or xenograft prostheses inside of or around the vein. However, such prostheses have not been devoid of problems leading to thrombosis and/or valve failure due to leaflet thickening/stiffening, non-physiologic flow conditions, non-biocompatible materials and/or excessive dilation of the vessels with a subsequent decrease in blood flow rates.

Percutaneous methods for treatment of venous insufficiency are being studied, some of which include placement of synthetic, allograft and/or xenograft prosthesis that suffer from similar problems as the surgically implanted ones discussed above.

In addition, venous valve formation from autologous tissue has been disclosed in U.S. Pat. No. 6,902,576 to Drasler et al. Drasler et al. suggests use of autologous tissue with blood contact of an endothelial layer to eliminate biocompatability issues and also alleviate thrombus formation due to low flow. However, methods of in situ venous valve formation according to Drasler et al. are surgical in nature and involve re-shaping a distended, diseased vein, which carries with it the risk of rupture or tearing of the thin-walled structure.

In view of the foregoing, there exists a need for methods and apparatus to restore normal venous circulation to patients suffering from venous valve insufficiency, wherein the methods and apparatus may be used in percutaneous, minimally invasive procedures. Further, such percutaneous methods and apparatus should attend to biocompatibility and thrombosis issues that current approaches do not adequately address.

BRIEF SUMMARY OF THE INVENTION

Embodiments hereof are directed to percutaneous methods and apparatus for creating monocuspid, bicuspid, and tricuspid venous valves from autologous tissue. One method disclosed herein includes obtaining percutaneous access to the lumen of a vein and tracking a catheter to a target location within the vein lumen where a venous valve is to be created in an antegrade manner, i.e., in the direction of antegrade blood flow. The catheter includes a radially-expandable component such as a balloon or braided member and at least one delivery shaft defining a delivery lumen and having a port that is positioned on one side of the radially-expandable component. A retractable dissecting system is slidingly received within the catheter. The dissecting system includes at least one expandable dissecting component that is constrained in a delivery configuration within the delivery lumen. After being advanced to the target location, the radially-expandable component of the catheter is expanded to bias the port against a wall of the vein. The retractable dissecting system is proximally retracted such that the at least one dissecting component exits the port formed within the delivery shaft, penetrates into the vein wall, and forms a subintimal longitudinal dissection of at least intimal tissue of the vein wall that is separated from remaining tissue of the vein wall. The dissecting component assumes an expanded configuration when it exits the port. The radially-expandable component of the catheter is collapsed such that the at least one dissecting component separates the subintimal longitudinal dissection of tissue from the remaining tissue of the vein wall and pulls the subintimal longitudinal dissection of tissue into a lumen of the vein, thereby simultaneously forming a flap of tissue and a sinus between the flap and the remaining tissue of the vein wall. The flap and the sinus constitute at least a portion of the venous valve.

In another method disclosed herein, the dissecting system includes at least one inflatable dissecting component that is constrained in a delivery configuration within the delivery lumen. The catheter is advanced to a target location within the vein lumen in the same manner as described above, and then the radially-expandable component of the catheter is expanded to bias the port against a wall of the vein. The retractable dissecting system is proximally retracted such that the at least one inflatable dissecting component exits the port formed within the delivery shaft and penetrates into the vein wall to form a subintimal longitudinal dissection of at least intimal tissue of the vein wall that is separated from remaining tissue of the vein wall. The at least one inflatable dissecting component is inflated within the vein wall to further dissect the at least intimal tissue of the vein wall from the remaining tissue of the vein wall, thereby simultaneously forming a flap of tissue and a sinus between the flap and the remaining tissue of the vein wall. The flap and the sinus constitute at least a portion of the venous valve.

Embodiments hereof are also directed to a system for creating a venous valve from autologous tissue, the system including a catheter having a radially-expandable component such as a balloon or braided member. The catheter includes at least one delivery shaft defining a delivery lumen and having a port that is positioned on one side of the radially-expandable component. A retractable dissecting system including a core element is slidingly received within a lumen of the catheter and includes at least one proximally-extending extension wire coupled to a distal end of the core element. The extension wire includes at least one expandable dissecting component that is slidingly disposed within the delivery lumen of the catheter. The expandable dissecting component is operable to exit the port to form a subintimal longitudinal dissection of a vein wall that separates at least intimal tissue from remaining tissue of the vein wall.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 1A-1B are schematic representations of blood flow through a healthy valve within a vein.

FIG. 2 is a schematic representation of blood flow through an incompetent valve within a vein.

FIG. 4A is a cross-sectional view of the balloon catheter of FIG. 4 taken along line A-A.

FIG. 4B is a cross-sectional view of the balloon catheter of FIG. 4 taken along line A-A according to another embodiment hereof.

FIG. 4C is a cross-sectional view of the balloon catheter of FIG. 4 taken along line C-C.

FIG. 4D is a sectional view of the balloon catheter of FIG. 4 taken along line D-D.

FIGS. 5A and 5B are side views of the distal portion of the balloon catheter of FIG. 4 according to alternative embodiments hereof.

FIGS. 15-19 are schematic representations of a method of forming a venous valve from autologous tissue in accordance with an embodiment hereof.

FIG. 20A is a schematic representation of a bicuspid venous valve formed in accordance with embodiments hereof.

FIG. 20B is a cross-sectional view of FIG. 20A taken along line B-B.

FIG. 21 is a schematic representation of the bicuspid venous valve of FIG. 20A including biasing elements in accordance with embodiments hereof.

FIG. 21A is a schematic representation of a tapered stent for use in venous valves formed in accordance with embodiments hereof.

FIG. 21B is a schematic representation of a biasing element for use in venous valves formed in accordance with embodiments hereof.

DETAILED DESCRIPTION OF THE INVENTION

Specific embodiments hereof are now described with reference to the figures, wherein like reference numbers indicate identical or functionally similar elements. The terms "distal" and "proximal" are used in the following description with respect to a position or direction of the balloon catheter and the retractable dissecting system relative to the treating clinician. "Distal" or "distally" are a position distant from or in a direction away from the clinician. "Proximal" and "proximally" are a position near or in a direction toward the clinician. With reference to venous valves and/or the flaps of tissue that form a venous valve, the term "proximal" refers to an end or portion in a direction toward the heart by way of blood flow path while the term "distal" refers to an end or portion in a direction away from the heart by way of blood flow path.

The following detailed description is merely exemplary in nature and is not intended to limit the invention or the application and uses of the invention. Although the description of the invention is in the context of treatment of blood vessels such as the deep and superficial veins of the leg, the invention may also be used in any other body passageways where it is deemed useful. Furthermore, there is no intention to be bound by any expressed or implied theory presented in the preceding technical field, background, brief summary or the following detailed description.

Figure 3:
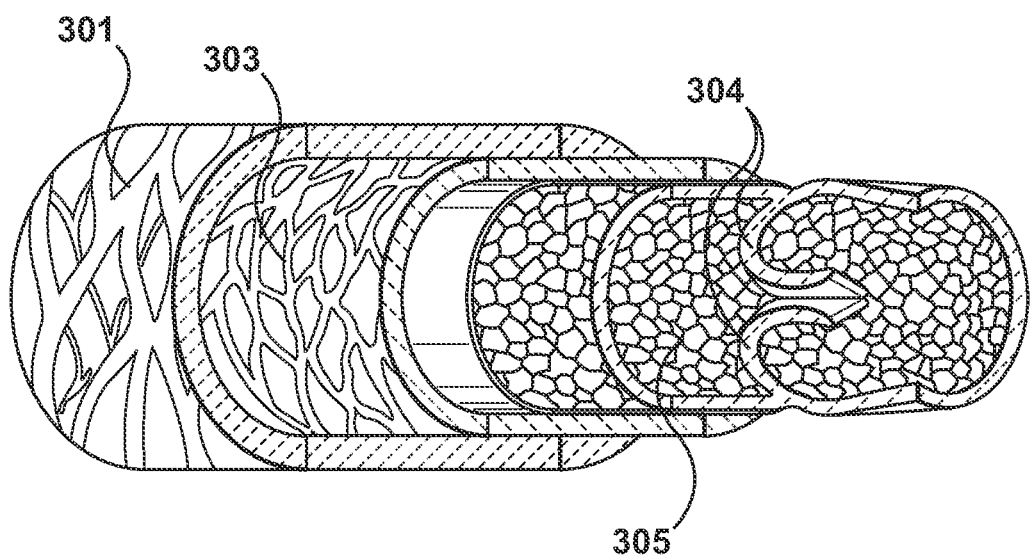
FIG. 3 is a sectional view of the anatomy of a healthy vein and valve thereof.

FIG. 3 depicts a sectional view of the anatomy of a vein wall, which for purposes of this description is shown to consist essentially of an outside layer 301, a middle layer 303 and an inside layer 305. Outer layer 301, or adventitia, is made of collagen, vasa vasorum and nerve cells. Middle layer 303, or media, is made of smooth muscle cells, whereas inner layer 305, or intima, is made up of endothelial cells. The endothelium provides a nonthrombogenic surface for flowing blood. Venous valve 304 having two leaflets is formed from folds of the inner or intimal layer such that both upstream and downstream blood contacting surfaces of valve 304 are covered with endothelium.

Figure 4:
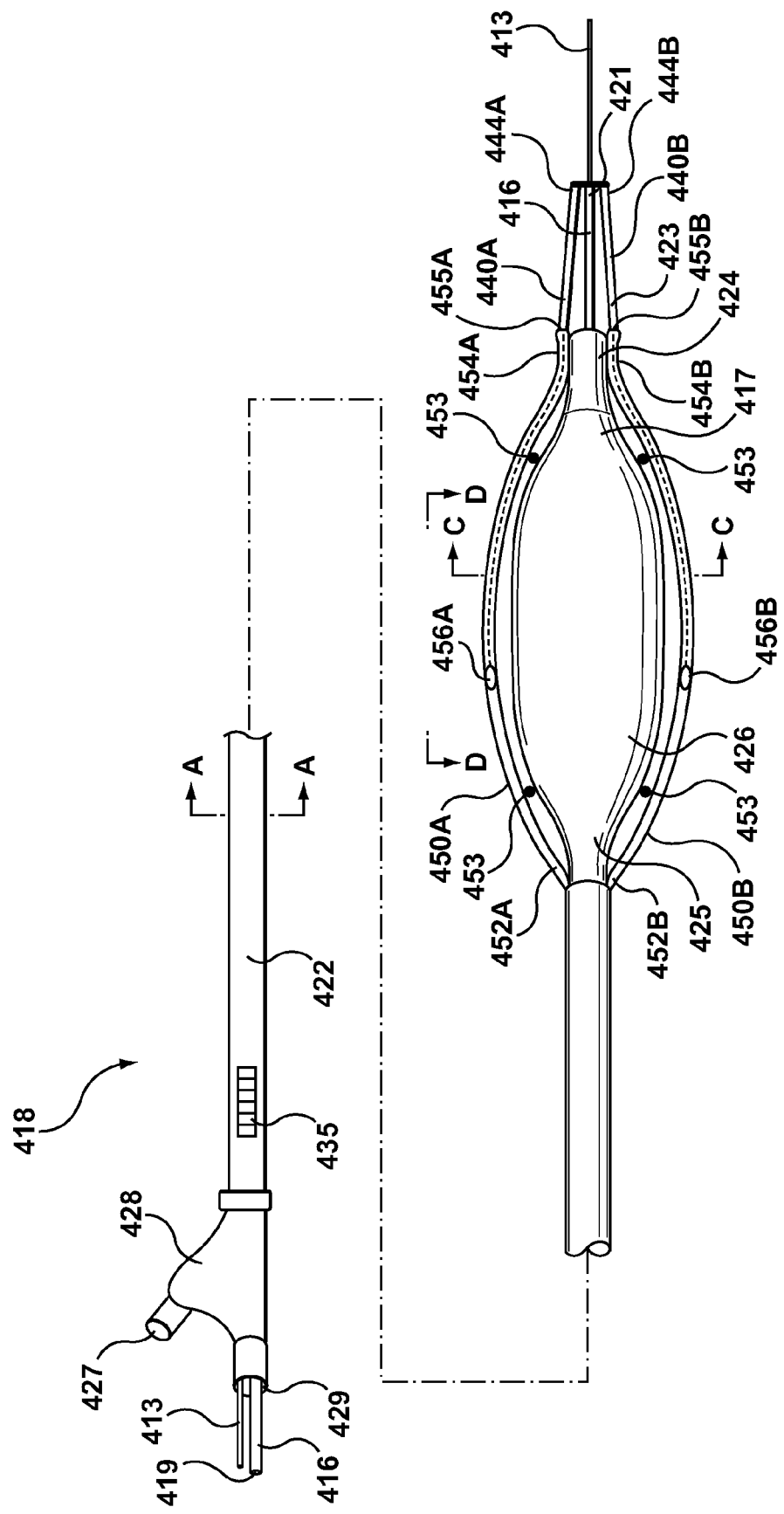
FIG. 4 is a side view of a balloon catheter in accordance with an embodiment hereof.
Figure 6:
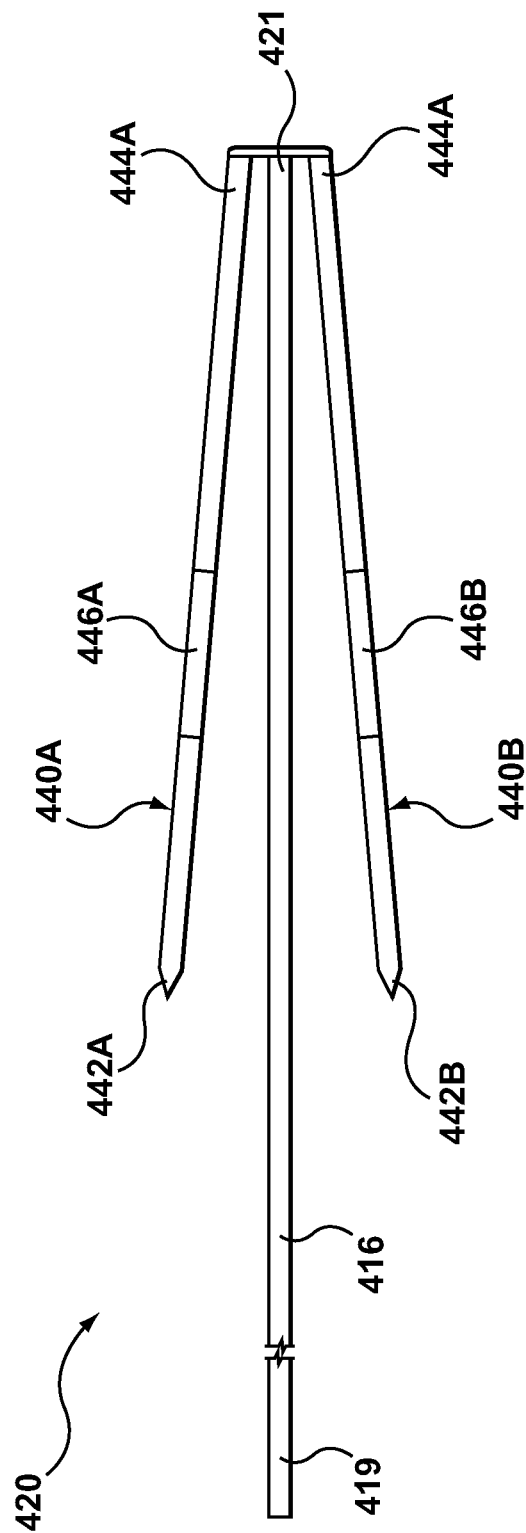
FIG. 6 is a side view of the retractable dissecting system of FIG. 4 removed from the balloon catheter.

According to one embodiment hereof, a retractable dissecting system 420 is slidingly disposed within a balloon catheter 418 for forming a venous valve from autologous tissue. FIG. 4 is a side view of dissecting system 420 disposed in a retracted position within balloon catheter 418, and FIG. 6 is a side view of retractable dissecting system 420 removed from balloon catheter 418 for illustrative purposes. Dissecting system 420 includes an elongated core element 416 and two proximally-extending extension wires 440A, 440B. Core element 416 may be a solid or hollow wire-like component having a generally circular cross-section as shown in FIG. 4A. Core element 416 has a proximal end 419 that extends proximally out of balloon catheter 418 and may be manipulated by a clinician, and a distal end 421 that extends distally out of balloon catheter 418. Extension wires 440A, 440B are relatively shorter solid or hollow wire-like components that extend in a proximal direction, i.e., towards proximal end 419 of core wire 416. Distal ends 444A, 444B, of extension wires 440A, 440B, respectively, are coupled to distal end 421 of core element 416 and proximal ends 442A, 442B of extension wires 440A, 440B, respectively, are sharpened or pointed tips that are operable to pierce into tissue. Along the length thereof between proximal tips 442A, 442B and distal ends 444A, 444B, each extension wire 440A, 440B includes an expandable dissecting component 446A, 446B (see FIG. 6) operable to access a sub-intimal space of a vessel wall and dissect or separate intimal issue from medial tissue as will be described in more detail herein with respect to FIGS. 15-19.

Extensions wires 440A, 440B may be integrally or continuously formed with cores shaft 416, or extension wires 440A, 440B may be separate formed and attached to distal end 421 of core element 416 in any suitable manner, including resistance welding, friction welding, laser welding, soldering, by the use of an adhesive, by the addition of a connecting element there between, or by another mechanical method. In one embodiment, core element 416 and/or extension wires 440A, 440B are solid or tubular components having outer diameters that range between 0.010 and 0.018 inches. Although shown as circular, core element 416 and/or extension wires 440A, 440B may have cross-sections known to those of ordinary skill in the art, including but not limited to circular, elliptical, rectangular, triangular, or other polygon. Suitable materials for use in forming core element 416 and/or extension wires 440A, 440B include stainless steel, nitinol (NiTi), nickel-cobalt alloy such as MP35N, cobalt-chromium, a relatively hard and sharp polymer, or a relatively hard and sharp ceramic material.

As shown in FIGS. 4, 4A, 4C, and 4D, core element 416 of dissecting system 420 is slidingly received through a central lumen 431 of balloon catheter 418 and extension wires 440A, 440B are slidingly received through two delivery shafts 450A, 450B positioned at the distal end of balloon catheter 418. More particularly, balloon catheter 418 includes a tubular outer shaft 422, an inner shaft 424, an inflatable balloon 426 positionable at a target location within the vasculature, and delivery shafts 450A, 450B coupled to the outer surface of balloon 426. Balloon 426 is shown in an expanded or inflated configuration in FIG. 4. Outer shaft 422 has a proximal end that extends out of the patient and is coupled to a hub 428, and a distal end coupled to a proximal end of balloon 426. Outer shaft 422 may be formed of a polymeric material, non-exhaustive examples of which include polyethylene, PEBA (PEBAX), and/or polyamide, and in an embodiment may include a reinforcement material such as braiding, wire mesh, or other wire members incorporated within a polymeric body in order to enhance strength and/or flexibility and torque response while preventing kinking of the shaft. Inner shaft 424 is an elongated tubular component defining at least central lumen 431 of inner shaft 424 for slidingly receiving core element 416 of retractable dissecting system 420 there through. In an embodiment depicted in FIGS. 4 and 4A, inner shaft 424 is a dual lumen shaft formed by multi-lumen profile extrusion and, in addition to central lumen 431, also defines a guidewire lumen 433 for slidingly receiving a guidewire 413 there through. In another embodiment shown in FIG. 4B, inner shaft 424B has a tubular body defining central lumen 431B for receiving core element 416B and core element 416B has a hollow tubular body defining guidewire lumen 433B for slidingly receiving guidewire 413. In an embodiment, inner shaft 424 may be formed from a flexible polymeric material, such as, e.g., polyethylene, polyamide, and/or polyether ether ketone (PEEK), and in an embodiment may include a reinforcement material such as braiding, wire mesh, or other wire members incorporated within a polymeric body in order to enhance strength and/or flexibility and torque response while preventing kinking of the shaft. In an embodiment, inner shaft 424 may be include one or more inner liners of polytetrafluoroethylene (PTFE) for central lumen 431 and/or guidewire lumen 433 to improve the slidability thereof. In yet another embodiment, inner shaft 424 may be formed from a hypotube of NiTi (nitinol) or stainless steel.

Inner shaft 424 has a proximal end that extends out of the patient and is coupled to hub 428 and a distal end that terminates distally of balloon 426, defining distal port 423 of balloon catheter 418. In the coaxial catheter construction of the illustrated embodiment, inner shaft 424 extends within outer shaft 422 such that an annular inflation lumen 430 is defined between an inner surface of outer shaft 422 and an outer surface of inner shaft 424. Other types of catheter construction are also amendable to the invention, such as, without limitation thereto, a catheter shaft formed by multi-lumen profile extrusion for defining an inflation lumen. Inflation lumen 430 allows inflation fluid received through an inflation port 427 of hub 428 to be delivered to balloon 426. As would be understood by one of ordinary skill in the art of balloon catheter design, hub 428 provides a luer hub or other type of fitting that may be connected to a source of inflation fluid and may be of another construction or configuration without departing from the scope of the present invention. In addition, hub 428 includes a port 429 that communicates with lumens 431, 433 of inner shaft 424 for slidably receiving retractable dissecting system 420 and guidewire 413, respectively, there through.

Each delivery shaft 450A, 450B is a tubular component that defines a delivery lumen 451A, 451B, respectively, there through for slidably receiving extension wires 440A, 440B, respectively, of retractable dissecting system 420. Delivery shafts of embodiments hereof may be made from any suitable material known to one of skill in the art of catheter construction, including by example, polyethylene, Polyimide, PEBAX, nylon, co-polyester elastomer, and PEEK. In the embodiment of FIG. 4, delivery shafts 450A, 450B include proximal ends 452A, 452B that are coupled to a proximal end 425 of balloon 426 and distal ends 454A, 454B defining distal ports 455A, 455B that are coupled to a distal end 417 of balloon 426. Delivery shafts 450A, 450B are positioned on opposing sides of balloon 426 or approximately 180° from each other with respect to the circumference of balloon 426. A proximal or side port 456A is disposed in a sidewall of delivery shaft 450A and is radially positioned on one side of balloon 426 and a proximal or side port 456B is disposed in a sidewall of delivery shaft 450B and is radially positioned on the other side of balloon 426 approximately 180° from proximal port 456A. Each of proximal ports 456A, 456B open so that when catheter 418 is placed within a vessel lumen each port faces an opposed surface of the vessel wall. In an embodiment, proximal ports 456A, 456B are longitudinally positioned at approximately the midpoint of the working length of balloon 426. However, the location of proximal ports 456A, 456B is not limited to the longitudinal position illustrated in FIG. 4, such that in other embodiments hereof proximal ports 456A, 456B may be positioned adjacent another longitudinal position along balloon 426 to include being positioned on or adjacent to proximal end 425 of balloon 426 or distal end 417 of balloon 426. As shown in the sectional view of FIG. 4D, each delivery shaft 450A, 450B may include a ramp 457A, 457B for directing instruments delivered through delivery lumens 451A, 451B toward a vein wall in vivo. Since ramps 457A, 457B are at an incline, they cause instruments delivered through delivery lumens 451A, 451B to be positioned outside of each delivery shaft 450A, 450B at an acute angle that may range from between 5° and 60° relative to the longitudinal axis of balloon 426. Proximally-extending extension wires 440A, 440B of retractable dissecting system 420 are slidably received through distal ports 455A, 455B of delivery shafts 450A, 450B, respectively, are disposed within delivery lumens 451A, 451B of delivery shafts 450A, 450B as best shown in the sectional view of FIG. 4D, and may be slidingly advanced through delivery shafts 450A, 450B such that proximal tips 442A, 442B exit proximal ports 456A, 556B via ramps 457A, 457B.

In one embodiment as shown in FIG. 4, delivery shafts 450A, 450B are detached from balloon 426 except at bonds 453 located adjacent balloon proximal end 417 and balloon distal end 425. In various embodiments, the bonds may be made by an adhesive or by creating a thermal bond between the materials of the components with, by e.g., heat shrink tubing. In such a configuration, semi-detached delivery shafts 450A, 450B do not interfere with the inflation of balloon 426. An optional stretchable sheath (not shown) may surround catheter 418 and hold the detached portions of delivery shafts 450A, 450B in apposition with balloon 426 during tracking of catheter 418 through the vasculature but may also allow for inflation of balloon 426 at the treatment site without being removed. The sheath would include side openings that correspond with proximal ports 456A, 456B to allow egress of extension wires 440A, 440B from delivery lumens 451A, 451B via the ports. In an embodiment, the sheath may be polyurethane or another elastomeric material and may be attached to the balloon by either a friction fit, with an adhesive, or thermal bonding the ends. In an alternate embodiment, shafts 450A, 450B may be attached along their length to the balloon working length.

FIGS. 5A and 5B depict alternative configurations of the delivery shafts for slidably receiving extension wires 440A, 440B, respectively, of retractable dissecting system 420. In the embodiment of FIG. 5A, delivery shafts 550A, 550B extend only over the distal half of balloon 426. More particularly, delivery shafts 550A, 550B extend only between proximal ends 552A, 552B defining proximal ports 556A, 556B located at approximately the midpoint of the working length of balloon 426 to distal ports 555A, 555B located at distal end 417 of balloon 426. Delivery shafts 550A, 550B may be attached along their length to the balloon working length as shown, or may be semi-detached from balloon 426 similar to delivery shafts 450A, 450B described above. In the embodiment of FIG. 5B, the delivery shafts are integrally formed within the material of the balloon rather than being attached to the outside surface of the balloon. More particularly, balloon 526 is a polymeric extrusion with delivery lumens 551A, 551B formed therein during the extrusion process. Extension wires of the retractable dissecting system are slidably received through distal ports 555A', 555B' and exit proximal ports 556A', 556B' located at approximately the midpoint of the working length of balloon 526.

In use, dissecting system 420 is operable to alternate between a retracted position in which extension wires 440A, 440B and dissecting component 446A, 446B are within delivery lumens 451A, 451B of delivery shafts 450A, 450B, and an exposed position in which extension wires 440A, 440B and dissecting component 446A, 446B extend transversely from proximal ports 456A, 456B of delivery shafts 450A, 450B until dissecting component 446A, 446B extend beyond an outer surfaces of delivery shafts 450A, 450B. To deploy or expose dissecting component 446A, 446B, core element 416 is proximally retracted within inner shaft 424 causing dissecting component 446A, 446B to also proximally retract within delivery shafts 450A, 450B and push against ramps 457 formed adjacent proximal ports 456A, 456B. Ramps 457 deflect extension wires 440A, 440B and dissecting component 446A, 446B through proximal ports 456A, 456B to the exposed or working position outside of delivery shafts 450A, 450B.

Figure 7:
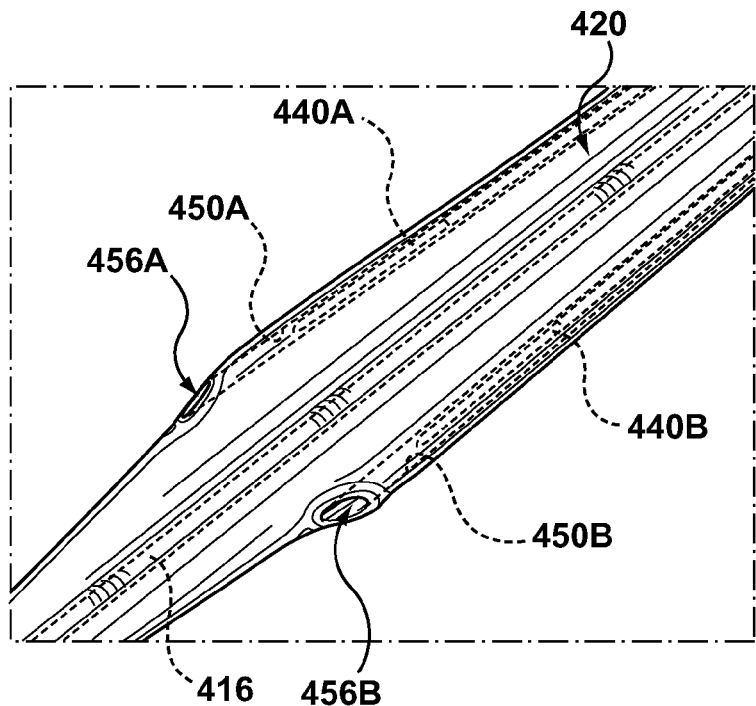
FIGS. 7-10 are perspective illustrations of the distal portion of the retractable dissecting system being deployed from the distal portion of the balloon catheter.
Figure 8:
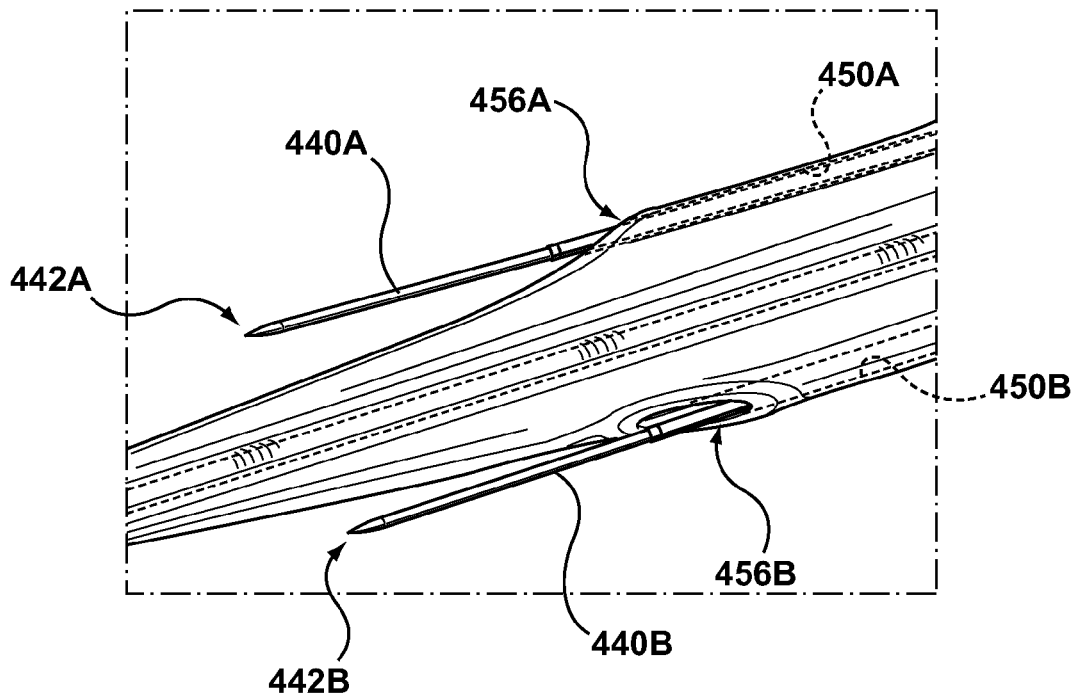
Figure 9:
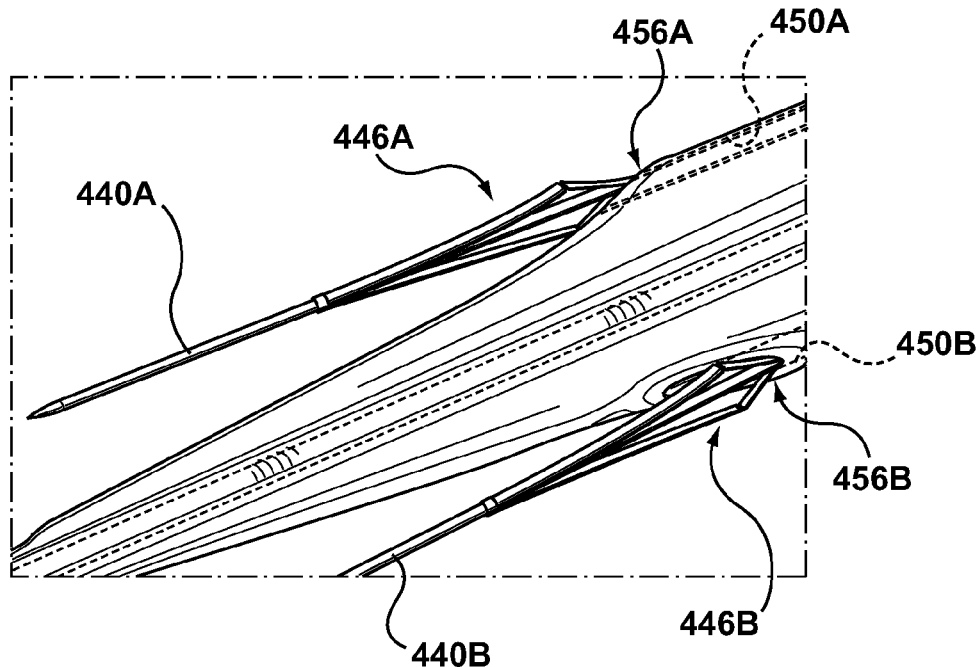
Figure 10:
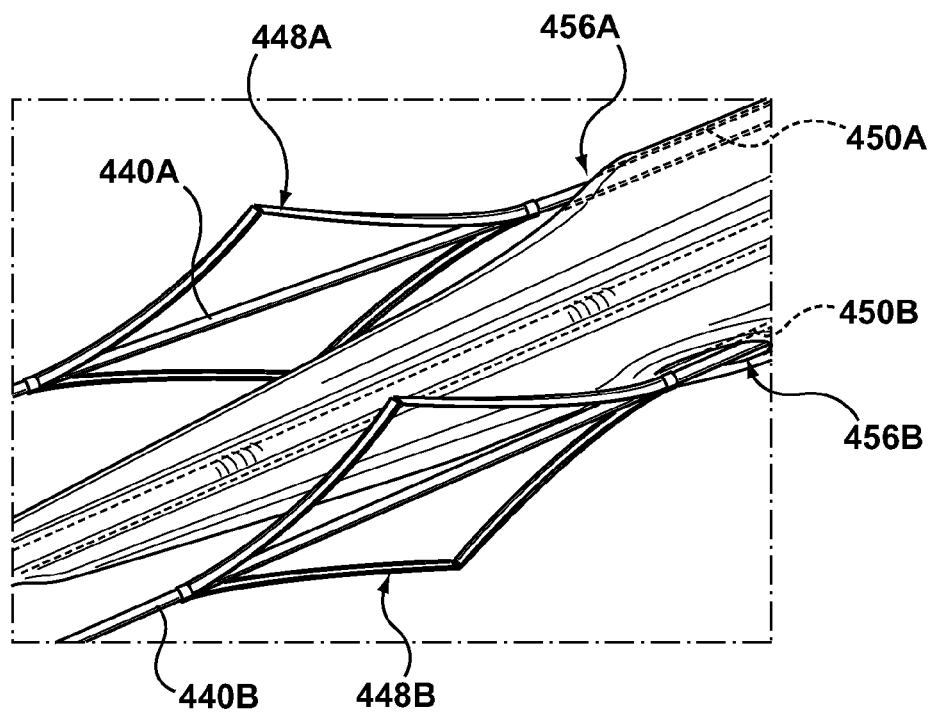
Figure 12:
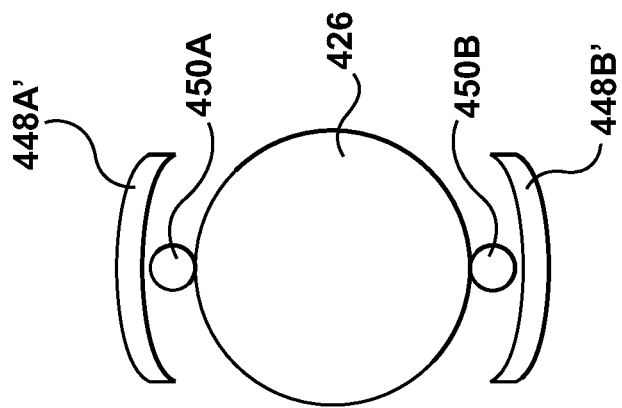
FIG. 12 is an end view of FIG. 4 according to an alternative configuration, showing the distal portion of the balloon catheter.
Figure 11:
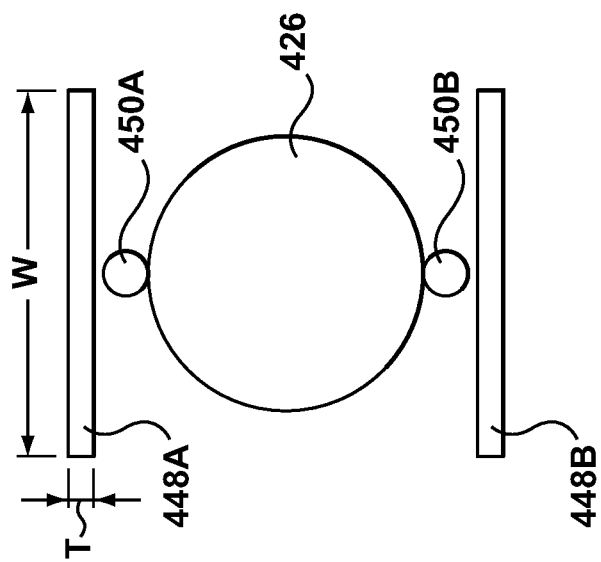
FIG. 11 is an end view of FIG. 4, showing the distal portion of the balloon catheter.

More particularly, FIGS. 7-10 illustrate deployment of dissecting component 446A, 446B through delivery shafts 450A, 450B. FIG. 7 illustrates extension wires 440A, 440B of retractable dissecting system 420 shown in the delivery lumens of delivery shafts 450A, 450B, respectively. Dissecting components 446A, 446B (not shown on FIG. 7) are compressed into a generally straightened delivery configuration. As core element 416 is proximally retracted or pulled, extension wires 440A, 440B, also move in a proximal direction until pointed tips 442A, 442B of extension wires 440A, 440B, respectively, exit out of proximal ports 456A, 456B of delivery shafts 450A, 450B as shown in FIG. 8. Continued proximal retraction of core element 416 results in dissecting component 446A, 446B being released or exposed from the delivery lumens of delivery shafts 450A, 450B as shown in FIG. 9 until dissecting component 446A, 446B are fully deployed into their preset configurations as shown in FIG. 10. In this embodiment, dissecting components 446A, 446B are diamond-shaped elements 448A, 448B. Diamond-shaped elements 448A, 448B are formed from a self-expanding material and are preset to splay outwardly and be radially spaced from extension wires 440A, 440B. "Self-expanding" as used herein means that diamond-shaped elements 448A, 448B have a mechanical memory to return to the expanded, deployed configuration shown in FIG. 10 from the straightened delivery configuration shown in FIG. 7. Mechanical memory may be imparted to diamond-shaped elements 448A, 448B by thermal treatment to achieve a spring temper in stainless steel, for example, or to set a shape memory in a susceptible metal alloy, such as nitinol. When expanded, each diamond-shaped element 448A, 448B has a rectangular or flat cross-section as shown in the end view of FIG. 11. In one embodiment, each diamond-shaped element 448A, 448B may have a width W that ranges between 4 and 15 mm, a thickness T that ranges between 0.1 and 0.5 mm, and a length that ranges between 4 to 15 mm. In another embodiment shown in the end view of FIG. 12, each diamond-shaped element 448A', 448B' may have a curved or semi-rounded cross-section that substantially corresponds to the outer surface or profile of inflated balloon 426. The curved cross-section of diamond-shaped elements 448A', 448B' may be beneficial when dissecting the intima from the vein wall in that the curved nature may enable them to more effectively cut through or "scoop" the curved vein wall.

Figure 13:
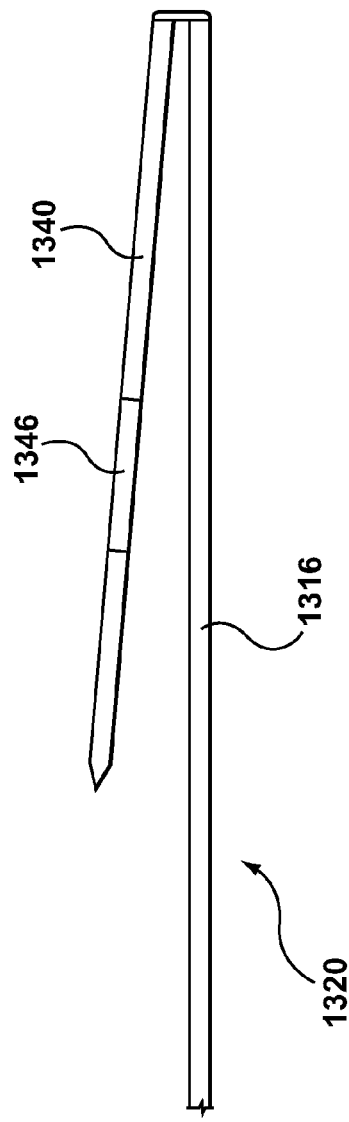
FIGS. 13-14 are side views of the retractable dissecting system removed from the balloon catheter having two and three dissecting components, respectively, in accordance with embodiments hereof.
Figure 14:
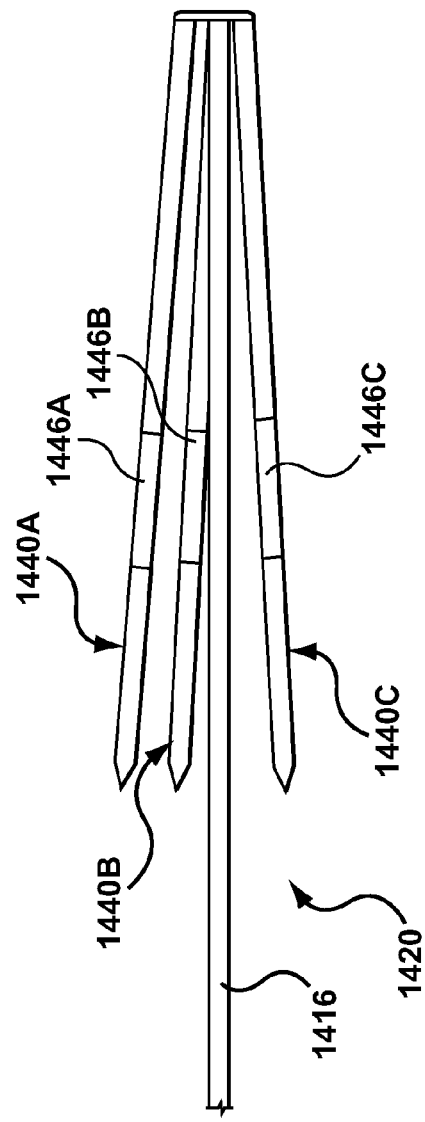

Although dissecting system 420 is shown as having two dissecting components 446A, 446B, the dissecting system may alternatively include one or three extension wire(s) and corresponding dissecting component(s), as shown in FIGS. 13 and 14 respectively. Specifically, as shown in FIG. 13, dissecting system 1320 includes core element 1316 and a single extension wire 1340 with dissecting component 1346 thereon which operates to create one intimal flap of tissue that functions as a monocusp leaflet as will be described in more detail herein. The balloon catheter for delivering dissecting system 1320 includes one delivery shaft for slidably receiving extension wire 1340. Similarly, FIG. 14 illustrates dissecting system 1420 includes core element 1416 and three extension wires 1440A, 1440B, 1440C with dissecting components 1446A, 1446B, 1446C respectively thereon which operate to create three intimal flaps of tissue that functions as tricusp leaflets. The balloon catheter for delivering dissecting system 1420 includes three delivery shafts for slidably receiving extension wires 1440A, 1440B, 1440C and the three delivery shafts may be located at equally-spaced radial positions around the circumference of balloon 426.

FIGS. 15-19 are schematic representations of a method of forming a venous valve from autologous tissue in accordance with an embodiment hereof, wherein the method includes utilizing dissecting components 446A, 446B of dissecting system 420 described above to create two intimal flaps of tissue from a vein wall which then act as a one-way valve in the manner of a native venous valve. The dissecting system described herein may be delivered to the target location in an antegrade manner. Antegrade delivery allows the dissecting system to easily and slidingly pass through the native valves without incidental damage thereto. In one embodiment, percutaneous luminal access to a desired peripheral vein 1500 is obtained through the popliteal vein or posterior tibial vein in the lower leg and delivery of the dissecting system is in an antegrade direction such that the dissecting system passes forwardly (i.e., distal to proximal relative to the heart) through native valves located within the vein in route to a target location where a new vein valve is to be created. In other embodiments, luminal access to desired peripheral vein 1500 is obtained through the greater or lesser saphenous, femoral, or popliteal veins using standard percutaneous techniques. It should be understood by one of skill in the art that methods as described herein may be used to form an autologous valve in any vein of sufficient thickness to enable a dissection to occur as described in greater detail below. Initially guidewire 413 may be maneuvered through the vasculature to rest across a target location within lumen 1515 of vein 1500 where a new venous valve is to be created. Balloon catheter 418 having deployable dissecting system 420 located therein is than advanced over guidewire 413 in an antegrade direction, i.e., in the direction of antegrade flow $A_F$, over the guidewire to the target location. If desired, a protective sheath 1560 may be provided to surround and cover balloon 426 and dissecting system 420 until deployment to facilitate tracking of balloon catheter 418 through the vasculature and prevent unintentional vessel damage while advancing dissecting system 420 to the target location. FIG. 15 illustrates balloon catheter 418 positioned at the target location, with balloon 426 in a delivery or non-inflated configuration and sheath 1560 partially retracted. Dissecting components 446A, 446B, are housed in a generally straightened delivery configuration within delivery shafts 450A, 450B, respectively.

Once positioned as desired, inflation fluid is provided via inflation port 427 (shown in FIG. 4) of hub 428 so that balloon 426 may be inflated as is known to one of ordinary skill in the art. As shown in FIG. 16, balloon 426 of catheter 418 is inflated to such an extent to press balloon 426, into apposition against the vascular wall of the vessel, i.e., fully positioned against or makes contact with the vessel wall. Delivery shafts 450A, 450B are also pressed against the vascular wall of the vessel, with proximal ports 456A, 456B thereof facing opposing surfaces of the vessel wall. Extension wires 440A, 440B of dissecting system 420 are still housed within the delivery lumens of delivery shafts 450A, 450B, respectively.

After balloon expansion, dissecting system 420 is proximally retracted in a direction indicated by arrow 1762 as shown in FIG. 17. As described above with respect to FIGS. 7-10, proximal retraction of core element 416 causes extension wires 440A, 440B to also move in the same proximal direction until pointed tips 442A, 442B of extension wires 440A, 440B, respectively, exit out of proximal ports 456A, 456B of delivery shafts 450A, 450B and puncture or pierce the intimal layer of the wall of vein 1500. Continued proximal retraction of core element 416 results in diamond-shaped elements 448A, 448B also exiting out of proximal ports 456A, 456B and deploying into their preset diamond-shaped configurations. Dissecting system 420 is proximally retracted a sufficient distance to allow diamond shaped elements 448A, 448B to create a subintimal longitudinal dissection of the intimal layer that separates tissue of the vein wall that substantially parallels a longitudinal axis of vein 1500. The subintimal longitudinal dissection may longitudinally extend within the intimal layer, between the intimal layer and the medial layer, between the medial layer and the adventitial layer, or within the medial layer; with care being taken that dissecting components 446A, 446B do not pass entirely through the vein wall.

Fluoroscopic or ultrasonographic guidance of retracting catheter 418 may be utilized to assure a length of the dissection plane created within the vein wall, as a length of the dissection plane will determine a length of the resulting flap. In one embodiment, at least dissecting components 446A, 446B are formed from a radiopaque material to aid in positioning the components within the vein wall. In another embodiment, radiopaque markers such as gold or platinum discs or bands may be placed onto extension wires 440A, 440B adjacent to pointed tips 442A, 442B and/or dissecting components 446A, 446B to aid in positioning the components within the vein wall. In order to make a bicuspid flap, each flap must have a free edge length of roughly half of the circumference of the vessel lumen with the depth of each dissection plane being sufficient to allow the resulting flaps to touch one another in the centerline of the vessel lumen. In order to make a monocuspid flap, the flap must have a free edge length of greater than half of the circumference of the vessel lumen with the depth of the dissection plane being sufficient to allow the resulting flap to touch the opposite side of the vessel wall. In order to determine an accurate depth/length of the dissection plane, an accurate measurement of the diameter of the vessel may be obtained by using fluoroscopy and quantitative coronary angiography (QCA). In such a procedure, the clinician uses a tool to "mark" the monitor with the fluoroscopic image. The tool has a calibrated measurement system so the clinician can accurately measure the diameter of the vein. Further, vessel diameter and wall thickness measurements may be obtained via intravascular ultrasound (IVUS), a medical imaging methodology that utilizes a miniaturized ultrasound probe attached to a distal end of a catheter to see from inside blood vessels out through the surrounding blood column. IVUS allows visualization of the inner wall of the vessel and thus the clinician may watch dissecting components 446A, 446B creating the dissection in real time. Alternatively, angiography with a road map may also be utilized to watch the vessel in real time or external ultrasound (Duplex) may be utilized to obtain information about the vessel diameter.

In addition, a series of depth markers 435 (see FIG. 4) may be located on the proximal portion of outer shaft 422 that extends outside of the patient's body in order to aid the physician in assessing how much to proximally retract catheter 418 to ensure that the appropriate length of tissue is dissected. Series of markers 435 may be spaced apart at predefined increments, such as for example between 1 mm and 5 mm apart. The location or position of the series of markers 435 on outer shaft 422 relative to a stationary object, such as a proximal hub of a guide catheter or sheath, may be monitored by the physician to track or measure how far catheter 418 is retracted during the cutting step of the procedure, thereby monitoring the length or depth of the dissection performed by dissecting components 446A, 446B situated near the distal end of catheter 418. The series of markers 435 may be printed on outer shaft 422 using pad-printing, laser printing, or other common printing techniques. Another method to monitor the length of the dissection includes placing a single marker such as an O-ring over the proximal portion of catheter 418. The single marker may be placed adjacent to or abutting against the insertion point of catheter 418 prior to performance of the dissection step. As catheter 418 is proximally retracted in order to create a dissection plane within the vein wall, the distance between the marker and the insertion point is monitored and measured to track the length of the dissection being formed by dissecting components 446A, 446B.

To complete the formation of the new venous valve after the dissection has been created in the vein wall, balloon 426 is subsequently collapsed or deflated such that the dissecting components 446A, 446B pulls or directs flaps 1832A, 1832B of tissue towards lumen 1515 of vein 1500 as shown in FIG. 18. In addition, deflation of balloon 426 may aid in further tearing the intimal flaps 1832A, 1832B so that they may function as a vein valve. The width W of dissecting components 446A, 446B, as well as the fact that dissecting components 446A, 446B extends from balloon 426 at angle Ø due to ramps 457A, 457B of delivery shafts 450A, 450B, causes flaps 1832A, 1832B of tissue to pull away from the vessel wall as balloon 426 is deflated to a smaller profile. Stated another way, deflation of balloon 426 essentially peels flaps 1832A, 1832B of tissue away from the remaining tissue of the vein wall. A flap by definition is a moveable piece of tissue partly connected to the body, and accordingly, it should be understood by the preceding description that a distal end of flaps 1832A, 1832B remain connected to the remaining tissue of vein 1500 while a proximal end or edge of flaps 1832A, 1832B are dissected away from the remaining tissue of the vein wall. When dissecting components 446A, 446B pull flaps 1832A, 1832B of tissue towards lumen 1515 of vein 1500, two pockets or sinuses 1834A, 1834B are simultaneously formed between flaps 1832A, 1832B and the remaining tissue of the vein wall. Sinuses 1834A, 1834B have a tapered shape in which a distal diameter thereof is smaller than a proximal diameter thereof. The tapered shape of sinuses 1834A, 1834B, which mimics native valve sinuses, aids in permitting blood to fill sinuses 1834A, 1834B and close flaps 1832A, 1832B. As mentioned previously, when referring to flaps 1832A, 1832B of tissue and other features of the venous valve, the term "proximal" refers to the end closest to the heart by way of blood flow path while the term "distal" refers to the end away from the heart by way of blood flow path.

In order to remove balloon catheter 418, retractable dissection system 420 is distally advanced in a direction indicated by arrow 1964 while holding balloon catheter 418 stationary to disengage dissecting components 446A, 446B from flaps 1832A, 1832B and reposition dissecting system 420 into the delivery lumens of delivery shafts 450A, 450B as shown in FIG. 19. Balloon catheter 418 and dissecting system 420 may then be proximally retracted and removed from the patient. If desired, sheath 1560 may be re-advanced over balloon catheter 418 and dissecting system 420 prior to proximally retracting and removing them from the patient.

In the embodiment of FIGS. 20A and 20B, flaps 1832A, 1832B include free edges 2036A, 2036B, respectively, that meet to close lumen 1515 in the absence of antegrade blood flow $A_F$, represented by arrow $A_F$, when retrograde or gravitational blood flow, represented by arrow $R_F$, fills sinuses 1834A, 1834B. When antegrade blood flow $A_F$ is once again present in vein 1500, and a pressure gradient exists such that $A_F > R_F$, flaps 1832A, 1832B are pushed away from each other, as shown in FIG. 20B, to allow blood flow through new venous valve 2014 on its way back to the heart. Flaps 1832A, 1832B are each of a sufficient length to permit free edges 2036A, 2036B of flaps 1832A, 1832B to touch against each other. In such an embodiment, flaps 1832A, 1832B and sinuses 1834A, 1834B constitute a bicuspid or two-leaflet venous valve 2014.

Figure 20C:
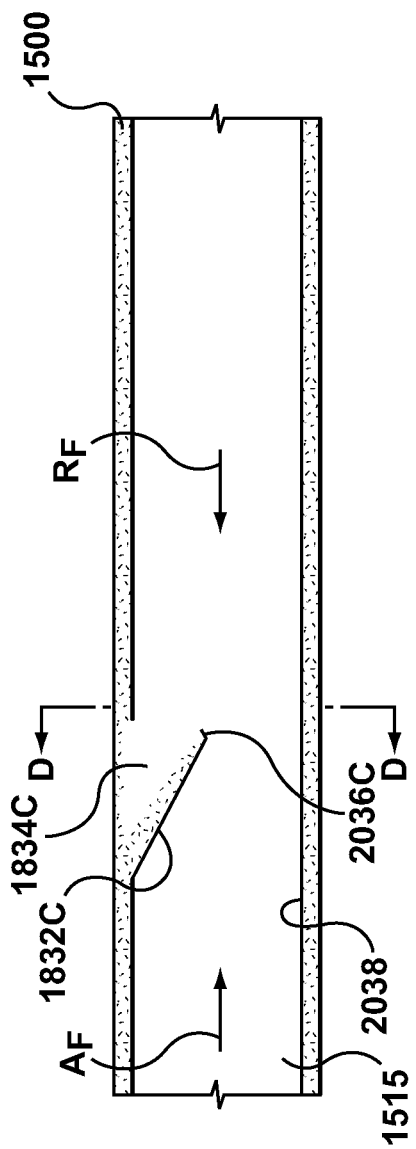
FIG. 20C is a schematic representation of a monocuspid venous valve formed in accordance with embodiments hereof.
Figure 20D:
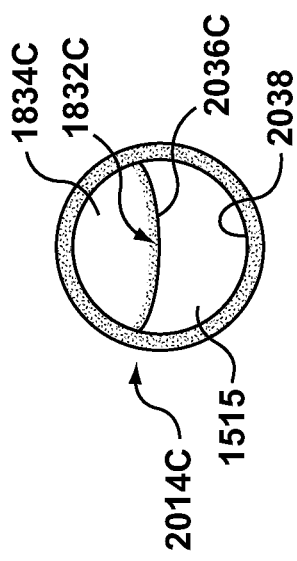
FIG. 20D is a cross-sectional view of FIG. 20C taken along line D-D.

In another embodiment hereof illustrated in FIGS. 20C and 20D, the dissecting system may include only one dissecting component for creating a single flap 1832C of intimal tissue as described above in relation to FIG. 13. Flap 1832C is of a sufficient length to make contact with an opposing side 2038 of the vein wall of lumen 1515, such that in the absence of antegrade blood flow, free edge 2036C of flap 1832C seals against opposing side 2038 while retrograde flow fills pocket 1834C. In such an embodiment, flap 1832C and pocket 1834C constitute a one-way monocuspid or one-leaflet venous valve 2014C of autologous tissue. Further, even if flap 1832C is not a sufficient length to fully extend across lumen 1515 and seal against opposing side 2038 of the vein wall, the presence of flap 1832C and pocket 1834C will significantly reduce the amount of blood that can reflux or backflow down the vessel. In another embodiment illustrated in FIG. 14, a total of three dissecting components may be deployed at equally-spaced radial positions around the circumference of balloon 426 in order to simultaneously form a tricuspid or three-leaflet valve.

In each of the aforementioned embodiments, the dissected flaps provide the same internal, i.e., facing the blood flow, tissue structure as a native valve thus providing a distinct advantage over prosthetic valve approaches. If the newly created flaps or leaflets 1832A, 1832B do not exhibit enough structural integrity to take the shape of a cusp or leaflet or if the flaps remain adhered to the remaining tissue of the vein wall the performance of those structures may be supplemented via biasing elements placed into pockets 1834A, 1834B. The biasing elements are designed to hold the shape of the pockets and do not offer much resistance to antegrade blood flow but instead collapse and allow the valve to open in the presences of antegrade flow. More particularly, with reference to FIG. 21, spring clip devices 2158A, 2158B may be placed into pockets 1834A, 1834B to aid in completely closing vessel lumen 1515 in the absence of antegrade blood flow $A_F$ by biasing flaps 1832A, 1832B against one and other. In this manner, retrograde blood flow $R_F$ is impeded from seeping through free edges 2036A, 2036B and causing reflux to instead fill pockets 1834A, 1834B. When antegrade blood flow $A_F$ once again pushes upon flaps 1832A, 1832B, spring clip devices 2158A, 2158B are compliant enough to compress to allow flaps 1832A, 1832B to part such that antegrade blood flows through bicuspid valve 2014. Spring clip devices 2158A, 2158B would be percutaneously delivered. In an embodiment the spring clips may be manufactured from a superelastic material such as nitinol. The clips may be shaped into a FIG. 8, as shown in FIG. 21B, and then folded at the mid-point to an appropriate angle, as shown in FIG. 21. In an embodiment, a suitable range for this angle is between 20 to 60 degrees. The spring-clip may be shape-set into this configuration using an oven set to an appropriate temperature for the material, by e.g., 525° C. for nitinol. The spring clip would then be loaded into a catheter assembly at the distal tip and advanced to the tissue pockets (sinus) in a retrograde direction. A pusher rod or other delivery mechanism may then be used to push the spring-clip out of the distal tip of the catheter and into the tissue pocket. Because of the materials superelasticity, the spring clip will self-expand to its original folded FIG. 8 configuration. Thus the material would contact the inner edge of the vessel wall and the inner edge of the created tissue pocket. In another embodiment, a tapered self-expanding stent 2159 as shown in FIG. 21A may be placed in each of pockets 1834A, 1834B to function in the same manner as previously described for spring clip devices 2158A, 2158B. Self-expanding stent 2159 may be made of nitinol with a very thin wall, such as having a wall thickness of between 0.001 to 0.005 inches.

Figure 22A:
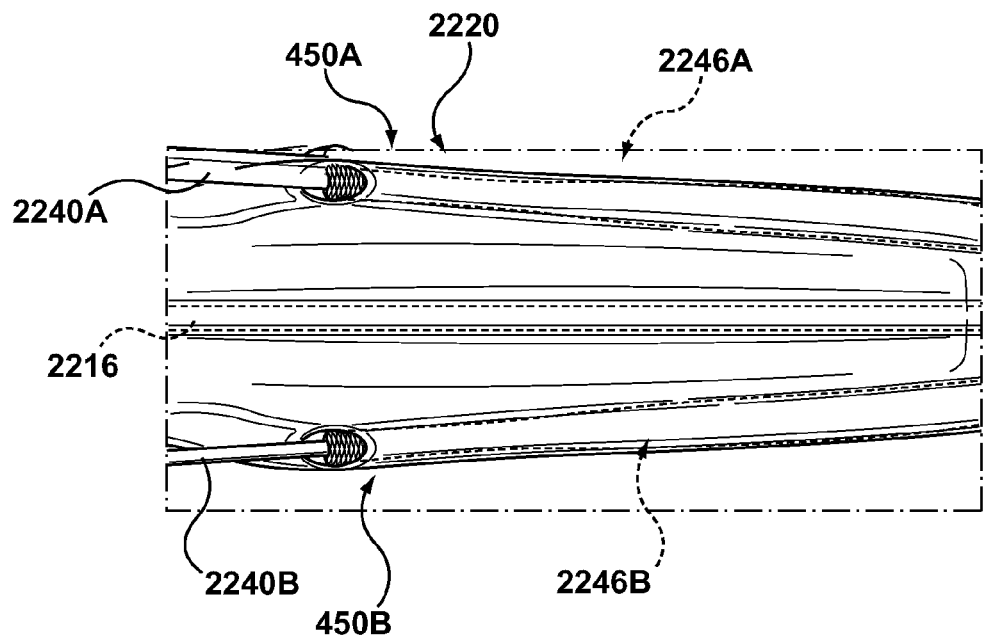
FIGS. 22A-22B are perspective illustrations of a distal portion of a retractable dissecting system being deployed from the distal portion of the balloon catheter, wherein the dissecting system includes radially-expandable braided dissecting components according to an embodiment hereof.
Figure 22B:
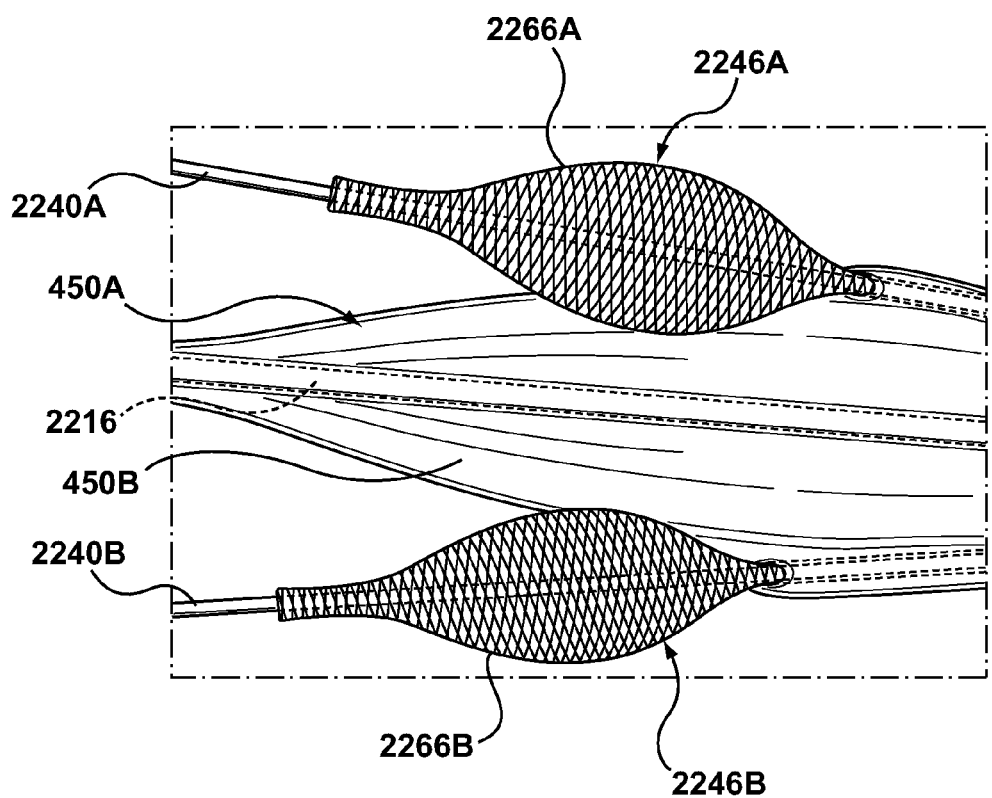

The expandable dissecting components may have alternative configurations from the diamond-shaped elements described above. For example, in another embodiment shown in FIGS. 22A and 22B, dissecting system 2220 includes a core element 2216 and two proximally-extending extension wires 2240A, 2240B coupled to the distal end (not shown) of core element 2216. Extension wires 2240A, 2240B include dissecting components 2246A, 2246B respectively that are self-expanding braided or mesh tubular components 2266A, 2266B constructed from a plurality of metallic or polymeric filaments woven together. In an embodiment, the filaments of braided tubular components 2266A, 2266B are formed from a self-expanding material including but not limited to stainless steel or a superelastic material such as NiTi (Nitinol) such that that braided tubular components 2266A, 2266B have a mechanical memory to return to the expanded, deployed configuration shown in FIG. 22B from the straightened or compressed delivery configuration shown in FIG. 22A. Thus, when dissecting system 2220 is proximally retracted, tubular components 2266A, 2266B are released or exposed from the delivery lumens of delivery shafts 450A, 450B until tubular components 2266A, 2266B are fully deployed into their preset radially-expanded configurations as shown in FIG. 22B. In the radially-expanded configuration, tubular components 2266A, 2266B may each approximate one of an ellipsoidal, spherical, and cylindrical-like shape. In operation, tubular components 2266A, 2266B expand or deploy into the sub-intimal layer and dissect the intimal layer from the media. In addition, in one embodiment, tubular components 2266A, 2266B in the expanded or deployed configuration may each have a sufficient outer diameter to dilate the sub-intimal space an adequate amount to create two intimal flaps of tissue and corresponding sinuses/pockets. Dissecting system 2220 is distally advanced in order to reposition tubular components 2266A, 2266B within the delivery lumens of delivery shafts 450A, 450B. Dissecting system 2220, as well as balloon catheter 418, may be retracted and removed from the patient.

Figure 23A:
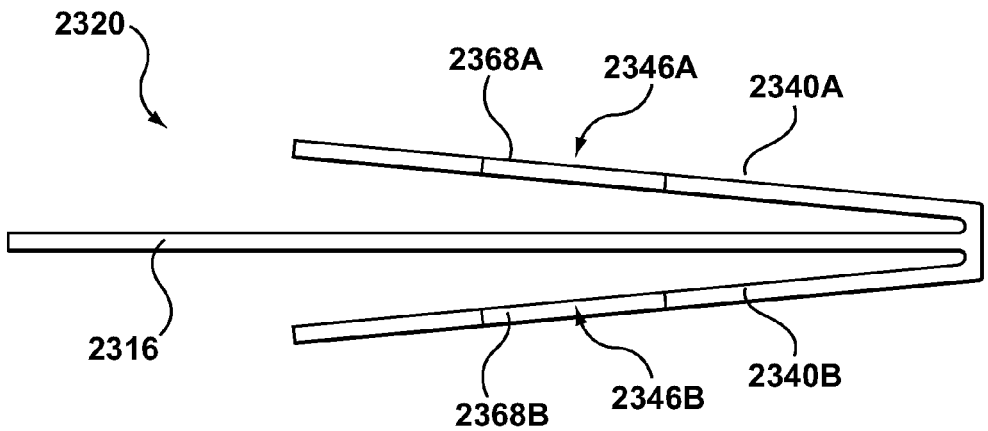
FIGS. 23A-23B are side views of a distal portion of a retractable dissecting system in a delivery configuration and an expanded configuration, respectively, wherein the dissecting system includes radially-expandable balloon dissecting components according to an embodiment hereof.
Figure 23B:
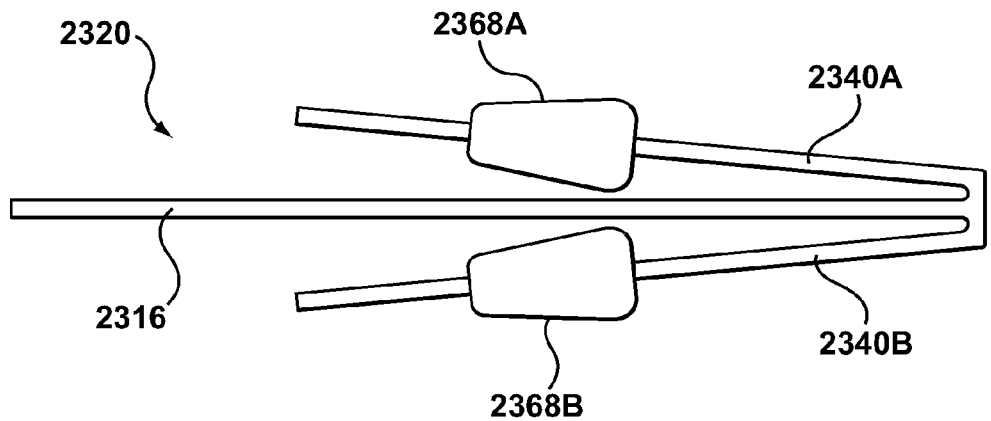

In another embodiment shown in FIGS. 23A and 23B, dissecting system 2320 includes a core element 2316 and two proximally-extending extension wires 2340A, 2340B coupled to the distal end of core element 2316. Extension wires 2340A, 2340B include dissecting components 2346A, 2346B respectively that are radially-expandable balloons 2368A, 2368B. In this embodiment, core element 2316 and extension wires 2340A, 2340B are each metallic or polymeric hypotubes defining lumens that are in fluid communication with each other such that inflation fluid injected through core element 2316 passes into extension wires 2340A, 2340B to inflate balloons 2368A, 2368B. In operation, dissecting system 2340 is proximally retracted until balloons 2368A, 2368B are no longer contained within the delivery lumens of the catheter delivery shafts and are properly positioned within the respective dissection planes made in the wall of the vein. Balloons 2368A, 2368B are simultaneously inflated within their respective dissection planes to expand or deploy within the sub-intimal space and dissect the intimal layer from the media. In addition, in one embodiment, balloons 2368A, 2368B may be expanded to a sufficient outer diameter to dilate the sub-intimal space an adequate amount to create two intimal flaps of tissue and corresponding sinuses/pockets. Balloons 2368A, 2368B are than deflated and dissecting system 2320 is distally advanced in order to reposition balloons 2368A, 2368B within extension wires 2340A, 2340B. Dissecting system 2320, as well as balloon catheter 418, may be retracted and removed from the patient.

As shown FIG. 23B, balloons 2368A, 2368B may have tapered shapes with a proximal inflated diameter that is smaller than a distal inflated diameter, wherein "proximal" and "distal" are used to describe a position relative to the treating clinician. The tapered shape of balloons 2368A, 2368B create conically shaped recesses between the dissected flaps of intimal tissue and the respective remaining medial tissue. The conically shaped recesses or spaces define pockets or sinuses and their shape, which mimics native valve sinuses, aids in permitting blood to fill the pockets and close the flaps of intimal tissue. An expanded proximal diameter of balloons 2368A, 2368B may be selected such that the resulting flaps are able to contact each other within the lumen in the absence of antegrade blood flow $A_F$.

Figure 24:
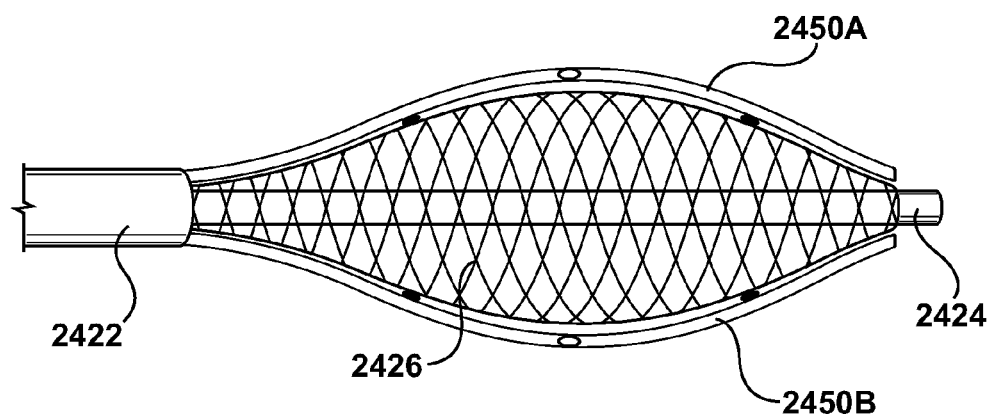
FIG. 24 is a side view of the distal portion of a delivery catheter having radially-expandable component according to alternative embodiments hereof.

In addition, the catheter described herein for delivering the dissecting system to the target location may have alternative configurations from the balloon catheter described above. For example, FIG. 24 depicts a distal portion of the catheter having a radially-expandable component that may be utilized in place of an inflatable balloon in embodiments described herein. More particularly, the delivery catheter may include an outer shaft 2422, an inner shaft 2424 concentrically disposed within outer shaft 2422, a braided or mesh tubular component 2426 constructed from a plurality of metallic or polymeric filaments woven together, and two delivery shafts 2450A, 2450B disposed over an outer surface of braided component 2426. A dissecting system such as dissecting system 420 described above is slidingly disposed through inner shaft 2424 and delivery shafts 2450A, 2450B in the same manner as described above with respect to inner shaft 424 and delivery shafts 450A, 450B. Further, delivery shafts 440A, 440B or 540A, 540B will be attached to the outer surface of braided component 2426 in the same manner as they were attached to the outer surface of balloon 426 described above. A proximal end of braided component 2426 is connected to a distal end of outer shaft 2422, and a distal end of braided component 2426 is connected to a distal end of inner shaft 2422. In one embodiment, braided component 2426 may be formed of a self-expanding material such as NiTi (Nitinol) such that when an outer sheath is retracted or pulled back, braided component 2426 resumes its radially-expanded configuration that contacts the vessel wall. In another embodiment, relative movement between outer and inner shafts 422, 424 radially expands braided component 2426 into apposition with the vessel wall and also straightens or collapses braided component 2426 into the delivery configuration after the retractable dissecting system forms a subintimal longitudinal dissection of at least intimal tissue of the vein wall. When fully expanded within the vessel, braided component 2426 may approximate one of an ellipsoidal, spherical, and cylindrical-like shape.

While various embodiments hereof have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope hereof should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An apparatus for creating a venous valve from autologous tissue, the apparatus comprising:
   a catheter having a radially-expandable component, wherein the catheter includes at least one delivery shaft defining a delivery lumen and having a port that is positioned on one side of the radially-expandable component; and
   a retractable dissecting system including a core element slidingly received within a central lumen of the catheter and at least one proximally-extending extension wire coupled to a distal end of the core element, wherein the extension wire includes at least one expandable dissecting component slidingly disposed within the delivery lumen and operable to exit the port to form a subintimal longitudinal dissection of a vein wall that separates at least intimal tissue from remaining tissue of the vein wall.

2. The apparatus of claim 1, wherein a proximal end of the extension wire includes a pointed tip.

3. The apparatus of claim 1, wherein the dissecting component is an expandable diamond-shaped component.

4. The apparatus of claim 1, wherein the dissecting component has a curved cross-section.

5. The apparatus of claim 1, wherein the dissecting component is an expandable tubular component constructed from a plurality of braided self-expanding filaments.

6. The apparatus of claim 1, wherein the dissecting component is an inflatable balloon having a tapered inflated shape with a proximal inflated diameter that is smaller than a distal inflated diameter.

7. The apparatus of claim 1, wherein the catheter includes first and second delivery shafts defining first and second delivery lumens and having first and second ports positioned on opposing sides of the radially-expandable component approximately 180 degrees from each other, and wherein the retractable dissecting system includes first and second dissecting components slidingly disposed within the first and second delivery lumens and operable to exit the first and second ports to form first and second subintimal longitudinal dissections of a vein wall that separate at least intimal tissue from remaining tissue of the vein wall.

8. The apparatus of claim 1, wherein the catheter includes first, second, and third delivery shafts defining first, second, and third delivery lumens and having first, second, and third ports positioned around the circumference of the radially-expandable component at approximately equally spaced intervals, and wherein the retractable dissecting system includes first, second, and third dissecting components slidingly disposed within the first, second, and third delivery lumens and operable to exit the first, second, and third ports to form first, second, and third subintimal longitudinal dissections of a vein wall that separate at least intimal tissue from remaining tissue of the vein wall.

9. The apparatus of claim 1, wherein the at least one delivery shaft includes a ramp formed therein adjacent to the port for deploying the at least one dissecting component through the port at an angle.

10. The apparatus of claim 1, wherein the radially-expandable component of the catheter is an inflatable balloon.

11. The apparatus of claim 1, wherein the radially-expandable component of the catheter is a tubular component constructed from a plurality of braided self-expanding filaments.

* * * * *